United States Patent [19]

Rivier et al.

[11] Patent Number: 5,807,986
[45] Date of Patent: *Sep. 15, 1998

[54] METHODS OF MAKING AND SCREENING BETIDE LIBRARIES

[75] Inventors: Jean E. F. Rivier, La Jolla; John S. Porter, Leucadia, both of Calif.

[73] Assignee: The Salk Institute For Biological Studies, La Jolla, Calif.

[ * ] Notice: The term of this patent shall not extend beyond the expiration date of Pat. No. 5,681,928.

[21] Appl. No.: 579,216

[22] Filed: Dec. 28, 1995

Related U.S. Application Data

[63] Continuation-in-part of Ser. No. 358,184, Dec. 16, 1994, Pat. No. 5,681,928.

[51] Int. Cl.$^6$ ...................................................... C07K 1/00
[52] U.S. Cl. .......................... 530/333; 530/324; 530/325; 530/326; 530/327; 530/328; 530/330; 530/334; 530/335
[58] Field of Search .................................... 530/333, 334, 530/335, 324, 325, 326, 327, 328, 330

[56] References Cited

U.S. PATENT DOCUMENTS

| | | | |
|---|---|---|---|
| 5,169,932 | 12/1992 | Hoeger et al. | 530/313 |
| 5,169,935 | 12/1992 | Hoeger et al. | 530/328 |
| 5,681,928 | 10/1997 | Rivier et al. | 530/333 |

OTHER PUBLICATIONS

Qasmi et al, "An–Aminoglycine Derivative Suitable for Soled Phase Pepitide Synthesis Using Fmoc Strategy", Tetrahedron Letters, vol. 34, No. 24, pp. 3861–3862, 1993.
Bock et al., "Differentially Protected–Aminoglycine", J. Org. Chem., vol. 51, No. 19, pp. 3718–3720, 1986.
Katrinzky et al., "Benzotriazole–assisted Synthesis of Monoacyl–Aminoglycines", J. Chem Soc. Chem. Commun., pp. 337–338, 1989.
Abstract, Koerber et al., "Solvation Energy Effects on the Conformation of Normal and Methylated Peptides and Betides", P505, *14th American Peptide Symposium*, Columbus, Ohio (Jun. 18–23/95).

Abstract, Rivier et al., "Betidamino Acids: Versatile and Constrained Scaffolds for Drug Discovery", L020, *14th American Peptide Symposium,* Columbus, Ohio (Jun. 18–23/95).

Abstract, Rivier et al., "Betidamino Acids: Versatile and Constrained Novel Scaffolds for Drug Discovery", Western Biotech Conference (Oct. 18–21, 1995).

*Primary Examiner*—Cecilia J. Tsang
*Assistant Examiner*—Anish Gupta
*Attorney, Agent, or Firm*—Fitch, Even, Tabin & Flannery

[57] ABSTRACT

Compounds termed "betides" mimic peptides and contain one or more residues of aminoglycine, $C^\alpha$-aminoalanine, aminosarcosine or the like wherein the side chain amino group has been acylated and optionally also alkylated. Generally, betides have the formula: $X_N$-$X_1$-$X_2$-$X_3$-$X_m$-$X_4$-$X_5$-$X_6$-$X_C$, where $X_N$ is an acyl or other N-terminal group or a peptide up to about 50 amino acids in length having such a group; $X_C$ is OH, $NH_2$ or other C-terminal group or a peptide up to about 50 amino acids in length having such a group; and $X_1$–$X_6$ are each independently a betidamino acid or α-amino acid or des-X; and $X_m$ is a peptide up to about 50 amino acids or des-X; provided however that at least one of $X_1$–$X_6$ is a betidamino acid residue having the formula:

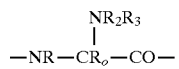

wherein $R_0$ is H or $CH_3$, R and $R_2$ are H or lower alkyl, and $R_3$ is an acyl group, an isocyanate or isothiocyanate group, a sulfonyl group or the like. To make a betide, an aminoglycine residue is subjected to side chain acylation, and optionally also alkylation, after it is coupled into a peptide intermediate. By synthesizing betides with multiple substituents at one or more positions in an otherwise peptidic chain, efficient screening of betides which mimic peptides having a large number of different natural or unnatural amino acid substituents at a particular position, and optionally both D- and L-isomers thereof, is possible.

12 Claims, No Drawings

METHODS OF MAKING AND SCREENING BETIDE LIBRARIES

This application is a continuation-in-part of application Ser. No. 08/358,184, filed Dec. 16, 1994, now U.S. Pat. No. 5,681,928.

This invention was made with Government support under grant numbers HD-13527, DK 26741, and contracts NO1-HD-3-3171 and NO1-HD-0-2906 awarded by the National Institutes of Health. The Government has certain rights in this invention.

This invention relates generally to unique amino acids termed betidamino acids, to peptides including such amino acids termed betides and to methods for making same, and particularly to methods for making libraries of betides using such unique amino acids as modular elements. It also relates to screening methods for testing whether substitutions of such unique amino acids (by virtue of their unique side chains) at particular positions in peptides of known biopotency will result in peptides having poorer, equivalent or improved properties. The information resulting from such screening of the effects of such side chain modifications is then also used to guide investigators in the design of other amino acids containing such side chains and similar analogs of the peptide being investigated.

BACKGROUND OF THE INVENTION

Peptide chemists have struggled for several decades to provide improved peptides that exhibit superiority, in at least one respect, to the corresponding native peptides. Generally this work involves tedious synthesis, by classical solution phase peptide synthesis or more efficient synthesis using solid phase peptide synthesis (SPPS), wherein other L-isomer or D-isomer amino acids, either natural or unnatural, are substituted one at a time for those which appear at particular locations in the native peptide or in an earlier developed analog thereof. For example, when one of skill in the art wishes to test the feasibility of substituting any one of, for example, five different amino acids in one position in a peptide sequence, it has heretofore been necessary to perform five different peptide syntheses to provide the 5 peptides for testing. Although this is feasible when the potential substituents are readily available natural amino acids or the like, oftentimes in an effort to improve the properties of peptides, peptide chemists have turned to using novel amino acids generally not commercially available. This frequently requires several arduous additional steps (i.e. the synthesis of the novel amino acid, its resolution and derivatization for synthesis), and when multiplied by five or more, it becomes extremely tedious. Thus, the current process of synthesizing multiple peptide analogs for biopotency testing is considered inefficient and costly.

Current academic and pharmaceutical research has also focused on the development of methodologies for generating chemical diversity (peptide or peptidomimetic libraries) for the discovery of new bioactive leads. In this respect, it has been shown that it may be efficacious to synthesize what have now been termed peptide libraries. This approach generally depends on automation of chemical methods for solid-phase syntheses and the identification of novel scaffolds. Several monomeric building blocks that mimic the peptide backbone have been proposed and include peptoids, azoles, 2-isoxazolines, oligocarbamates, oligosulfones and oliogsulfoxides, pyrrolinones, vinylogous backbones, β-methyl amino acids and the more classical oligomers with pseudopeptide bonds. As one example, multiple selected natural amino acids may be coupled at one or at several preselected locations along a growing peptide chain to create multiple peptides of diverse composition.

In addition to the difficulty faced by those of skill in the art in designing peptide-based drugs, such persons have also been forced to deal with concerns regarding degradation and insolubility. Because the ultimate goal of peptide syntheses are therapeutic compositions for use in the treatment of various diseases, such as hormone deficiency disorders, persons designing and synthesizing such peptides must consider both the method of administration of the therapeutic agent and its subsequent stability within the human body. Peptides with increased hydrophilicity have certain distinct advantages because they are more soluble in biological solutions making their administration easier. Often such peptides will need to have their hydrophilicity profile fit within a narrow range in order to make their long term administration feasible. Similarly, peptides with decreased susceptibility to enzymatic degradation are very often preferred because they remain effective in the human body for longer periods of time.

Attempts have also been made to provide peptides with increased stability, and it is well known to those of skill in the art that certain unnatural amino acids provide peptides with enzymatic stability. For example, one group of peptides with increased stability is "geminal peptides", wherein one or more of the peptide amide groups is reversed, that is, CHRCONH is modified to CHRNHCO—see e.g. Katritzky, et al. *J. Org. Chem.* 55;2206–2214 (1990). Another group of peptides with increased stability includes those mentioned above which are termed "peptoids". Peptoids are peptides wherein the normal side chain group of the α-amino acid is located on the nitrogen atom of the α-amino group rather than on the α-carbon atom—see Simon, et al., *P.N.A.S.* 89:9367–9371 (1992). However, none of the above described peptides can be synthesized more efficiently than peptides containing the usual derivatized amino acids (natural and unnatural).

The search has continued for new amino acids that increase the biopotency or improve other properties of peptides. Moreover, more efficient and economical methods continue to be sought for generating novel peptides, particularly large numbers of peptides, useful in screening for novel activities, for increased biopotency or for other preferred properties.

SUMMARY OF THE INVENTION

The present invention provides betide amino acids or betidamino acids which are mono-acylated aminoglycine derivatives, wherein the side chain resembles a natural amino acid side chain, and which generally mimic an α-amino acid either with or without a lower alkyl (e.g. methyl) substitution on the β-carbon atom. The α-amino group in the backbone can also be optionally alkylated. Such betidamino acids can be incorporated into peptides, herein termed "betides", which have improved and/or unique properties relative to comparable natural peptides and/or peptides made up of residues of only non-betidamino acids. Very importantly, screening using such betides can be utilized to provide valuable information for use in designing novel peptides which contain only non-betidamino acids, as well as to discover valuable betides.

Betides can be synthesized by utilizing a building block in the form of a bis-protected α-amino-glycine (or α-aminoalanine or α-aminosarcosine) in a conventional chain elongation process, which building blocks may also be bis-methylated. The amino function that is not part of the backbone is referred to as the beta-site amino group, and it is preferably acylated after being incorporated into the backbone and then being selectively deprotected. Acylation is accomplished with carboxylic acids (with a coupling agent), active esters or anhydrides, mixed or symmetric, or with an acyl chloride. Alternatively, a reaction (herein broadly termed acylation) can be carried out with an isocyanate, an isothiocyanate, or a sulfonyl chloride to affect similar substitution in the beta-site amino side chain. When the beta-site amino group is disubstituted, the other substituent is preferably an alkyl moiety which is herein defined to include a substituted alkyl group.

Betidamino acids and/or betides generally have 3 unique and desired properties compared, for example, to natural amino acids and peptides including only such natural residues. They have increased solubility at normal physiological pH compared to the corresponding natural amino acid or to the peptide incorporating the corresponding natural amino acid at that position as evidenced by the fact that betides elute earlier on RP-HPLC than their corresponding peptides. In a betide, there is a unique preference (constraint) of three-dimensional side chain orientation, which is quite limited as compared to that of a residue of the corresponding natural amino acid in the same position in the backbone but which is found to be very similar to the space occupied by $C^\beta$-methyl amino acids, that are unilaterally very difficult to synthesize. This property is particularly valuable for facilitating the design of highly specific peptides, i.e. analogs that bind to only one receptor subtype when several subtypes are known to exist. The number of novel betidamino acids and betides that can be made is limited only by the number of existing acylating agents, of which there are thousands, thereby allowing almost unlimited versatility in the design of such new compounds.

Of particular interest are betidamino acids which have side chains that resemble the structures of natural amino acids other than glycine. Generally, these betidamino acids can be incorporated into peptides being made by chain-elongation synthesis in the same manner as any protected known α-amino acid. However, in some instances, there may be advantages to forming the desired betidamino acid within a peptide chain or within a peptide intermediate that is still attached to a resin or in solution.

Although preparation of individual betides for screening is considered valuable, a synthesis strategy can also be employed wherein a bis-protected aminoglycine or the like is incorporated into a desired position in a peptide chain, and then a plurality of different modifications (alkylation, acylation or the like) are effected in the residue at this particular position in the peptide chain, to prepare multiple betides for subsequent screening for activity, biopotency and other properties. For example, a particular precursor peptide is synthesized having a protected aminoglycine residue at a desired position in the chain. The beta-site amino group of this residue is then selectively deprotected and acylated using a plurality of acylating agents. Such a procedure allows one to independently or simultaneously prepare an entire array of betides for screening for biopotency or any other desirable peptide property, wherein such individual betides have different substituents at the aminoglycine residue due to the plurality of acylating agents employed. In addition, the beta-site amino groups may also be alkylated using a plurality of alkylating agents.

By using a plurality of aminoglycine residues in a single backbone, an even larger number of different betides can be created that will each have 2 or 3 or more betidamino acids. Such is preferably carried out by solid phase synthesis (SPPS) using individual wells or plates or pins or using a bed of resin beads. For example, if during a solid-phase synthesis, beads of resin are divided into 10 different portions which are then reacted with ten different acylating agents, by recombining the beads, mixing them and then either adding another protected aminoglycine residue or separately deprotecting another aminoglycine residue already in the chain, the acylation process can be repeated after again dividing the group into 10 portions. Such separate reaction again with 10 different acylating agents would produce 100 different compounds because each of the 10 original intermediates would be subsequently modified in 10 different ways to create 100 different intermediates. By repeating the sequence a third time by treating the recombined group of beads, either by coupling a third aminoglycine residue into the chain or by suitably sequentially deprotecting a third aminoglycine residue which was earlier incorporated within the chain, then dividing it again into 10 portions and reacting with 10 different acylating agents, the 100 intermediates are transformed into 1,000 different betide intermediates. Thus, the invention provides a preferred way of creating a useful library of great diversity.

Such libraries allow the identification of compounds that will be themselves directly useful pharmacologically or which will provide good leads for drug discovery.

DETAILED DESCRIPTION OF THE PREFERRED EMBODIMENTS

The terms used herein are conventional to the field of the invention and so are generally defined as known to those of skill in the art. Peptide sequences are described according to the convention of naming the amino terminus first and the carboxyl terminus last.

The present invention provides betidamino acids, which are mono-acylated versions of aminoglycine (Agl) or α-aminoalanine (Aal) or α-aminosarcosine (Asa) or bis-methylated diaminoglycine (Mdg) or bis-methylated diaminoalanine (Mda) wherein the N- or alpha-amino site is destined to become part of the backbone of the peptide chain of residues and the N'- or beta-amino site is substituted as with an acyl group that resembles a natural α-amino acid side chain so that the betidamino acid generally mimics the α-amino acid. Either one or both of the amino functions of Agl or Aal can be optionally alkylated prior to acylation. Acylation of the beta-amino site with a suitable carboxylic function produces a stable amide linkage which cannot be selectively cleaved without cleaving peptide bonds in the backbone. Although for convenience of description the term acylation is generally used throughout this specification, it should be understood other amino-reactive reagents can instead be used that will create a similarly stable linkage; for example the beta-site amino group may be alternatively substituted by an isocyanate, an isothiocyanate, a sulfonyl chloride or the like. As used herein, the term "betide" refers to a peptide containing one or more betidamino acid residues, which are mono-acylated residues as defined above, which can be non-, mono- or di-alkylated, wherein the acyl (or other) substitution at the beta-site is stable under synthesis conditions as defined above. For example, either, both or neither of the amino groups may be methylated.

A subclass of substituted α-aminoglycines which are useful in constructing betides are herein given the shorthand nomenclature b-Xaa, where Xaa is the three-letter abbreviation for a known amino acid particularly-one of the natural α-amino acids. Appropriate acylating agents are incorporated to create side chains that closely resemble the side chains of the known amino acids (with the exception of glycine which lacks any side chain), and in some instances a lower alkyl group (e.g. methyl or ethyl) is substituted on the β-site amino group. In all these betidamino acids, the side chain amide bond (HN—C=O) corresponds by definition to the β CH$_2$ (methylene) in the native amino acid. In some instances, however, the amide bond may have such effect that the particular betidamino acid is generally isosteric with a homologous α-amino acid (for example, betidevaline and isoleucine). In some instances there may also be a steric resemblance to the C$^β$ methyl-substituted α-amino acid. An "h", as in b-hXaa, indicates that the side chain is a homolog having one additional carbon atom in comparison to the side chain of the designated natural α-amino acid; however, from a certain viewpoint it may more closely resemble the structure of the corresponding natural amino acid side chain. For example, b-hCys has the structure:

$$\begin{array}{c} HS-CH_2 \\ | \\ C=O \\ / \\ HN \\ | \\ H_2NCHCOOH \end{array}$$

and may be named as γ-(thiolmethyl)amidoglycine. The prefix "n" indicates that the resemblance is closer to a "nor" version of the natural α-amino acid, i.e. shortened by one methylene group. Although the specified side chain structurally resembles that of the corresponding natural α-amino acid, the configuration of certain of these residues in a betide may more closely resemble the three-dimensional configuration of a C$^β$-methyl natural amino acid, as explained hereinbefore, making them particularly valuable and useful for this reason.

The following is a list of betidamino acids (substituted α-aminoglycines) which have been designed so that each side chain mimics the side chain of the natural or other well known α-amino acid that is incorporated in the betide nomenclature in the left-hand column:

b-Ala=H$_2$NCH(NHC(O)H)COOH=amidoglycine or formyl-aminoglycine b-hAla=H$_2$NCH(NHC(O)CH$_3$)COOH=γ-methylamidoglycine or acetyl-aminoglycine b-Leu=H$_2$NCH(NHC(O)CH(CH$_3$)$_2$)COOH=γ-isopropylamidoglycine b-Val=H$_2$NCH(NCH$_3$C(O)CH$_3$)COOH=β,γ-dimethylamidoglycine; also considered to constitute Ile isostere b-Ile=H$_2$NCH(NCH$_3$C(O)CH$_2$CH$_3$)COOH b-hSer=H$_2$NCH(NHC(O)CH$_2$OH)COOH=γ-(hydroxymethyl)amidoglycine b-hThr=H$_2$NCH(N(CH$_3$)C(O)CH$_2$OH)COOH=γ-methyl(hydroxymethyl)amidoglycine b-hCys=H$_2$NCH(NHC(O)CH$_2$SH)COOH=γ-(thiolmethyl)amidoglycine b-Met=H$_2$NCH(NHC(O)CH$_2$SCH$_3$)COOH=γ-methylthiomethylamidoglycine b-Phe=H$_2$NCH(NHC(O)C$_6$H$_5$)COOH=γ-phenylamidoglycine b-Tyr=H$_2$NCH(NHC(O)C$_6$H$_4$OH)COOH=γ-(4-hydroxy)phenylamidoglycine b-Trp=H$_2$NCH(NHC(O)C$_8$H$_5$NH)COOH=γ-indolylamfidoglycine b-Lys=H$_2$NCH(NHC(O)CH$_2$CH$_2$CH$_2$NH$_2$)COOH; also considered to constitute homoLys isostere b-nArg=H$_2$NCH(NHC(O)CH$_2$NHC(=NH)NH$_2$)COOH=γ-methylguanidinoamidoglycine; also considered to constitute Arg isostere b-Arg=H$_2$NCH(NHC(O)CH$_2$CH$_2$NHC(=NH)NH$_2$)COOH=γ-ethylguanidinoamidoglycine b-His=H$_2$NCH(NHC(O)C$_3$N$_2$H$_3$)COOH=γ-imidazolylamidoglycine b-Asp=H$_2$NCH(NHC(O)COOH)COOH=γ-carboxyamidoglycine; also considered to constitute Glu isostere b-Asn=H$_2$NCH(NHC(O)CONH$_2$)COOH=γ-amidoamidoglycine; also considered to constitute Gln isostere b-Glu=H$_2$NCH(NHC(O)CH$_2$COOH)COOH=γ-(carboxymethyl)amidoglycine; also considered to constitute homoGlu isostere b-Gln=H$_2$NCH(NHC(O)CH$_2$CONH$_2$)COOH=γ-(carboxamidomethyl)amidoglycine; also considered to constitute homoGln isostere $$b\text{-nPro} = \begin{array}{c} O=C\text{——}NH \\ | \quad\quad\quad | \\ CH_2 \quad CH-COOH \\ \backslash \quad / \\ NH \end{array} = \text{4-keto-tetrahydroimidazol-2-carboxylic acid}$$

$$bPro = \begin{array}{c} \quad\quad\quad O \\ \quad\quad\quad \| \\ CH_2-C-NH \\ | \quad\quad\quad | \\ CH_2 \quad CH-COOH \\ \backslash \quad / \\ NH \end{array}$$

An isostere is a molecule which has the same steric configuration as another so that it occupies the same 3-dimensional space.

It can be seen that this novel methodology also gives easy access to equivalent amino acids relative to those α-amino acids having extended side chains such as homo-Xaa, homo-homo Xaa, etc.

The term "natural amino acid group", is used herein to refer to the following group of sixteen α-amino acids: alanine (Ala), valine (Val), leucine (Leu), isoleucine (Ile), lysine (Lys), arginine (Arg), histidine (His), proline (Pro), phenylalanine (Phe), tyrosine (Tyr), tryptophan (Trp), aspartic acid (Asp), glutamic acid (Glu), asparagine (Asn), glutamine (Gln) and methionine (Met)—from which glycine (Gly), serine (Ser), threonine (Thr) and cysteine (Cys) have been omitted.

The term "unnatural amino acid" as used herein refers to all α-amino acids which are not natural α-amino acids. This includes for example betidamino acids, as defined above, beta-methyl α-amino acids and other derivatives and homologs of natural amino acids, such as ornithine (Orn), norleucine (Nle), pyridylalanine (PAL), γ-(2-naphthyl)-D-alanine (γ-D-2NAL), N$^ε$-5'-(3'-amino-1H-1',2',4'-triazolyl) lysine (Lys(atz)), and the like. Betidamino acid forms of these unnatural α-amino acids include:

b-Abu=H$_2$NCH(NCH$_3$C(O)H)COOH=β-methylamidoglycine; also considered to constitute Val isostere b-Nle=H$_2$NCH(NHC(O)CH$_2$CH$_2$CH$_3$)COOH=γ-propylamidoglycine, b-Orn=H$_2$NCH(NHC(O)CH$_2$CH$_2$NH$_2$)COOH=γ-(2-aminoethyl)amidoglycine; also considered to constitute Lys isostere b-PAL=H$_2$NCH(NHC(O)C$_5$NH$_4$)COOH=γ-pyridylamidoglycine, b-NAL=H$_2$NCH(NHC(O)C$_{10}$H$_7$)COOH=γ-naphthylamidoglycine, b-Cpa=H$_2$NCH(NHC(O)C$_6$H$_4$Cl)COOH=γ-4-chlorophenyl-amidoglycine, and b-Fpa=$H_2NCH(NHC(O)C_6H_4F)COOH$=γ-4-fluorophenyl-amidoglycine As used herein, the term "betide library" refers to an array that has been created which includes a plurality of different analogs of biologically active peptides or peptides with other unique properties wherein at least one residue in each analog compound in the array is a betidamino acid and wherein a variety of different betidamino acid residues are present in the array. One or more intermediate peptides or peptidoresins for producing such betide libraries may be synthesized and then maintained, e.g. as a stock solution or stock peptide resin from which a plurality of such different analogs can be made for use in screening to determine the effect of such substitutions upon biopotency or upon some other activity or property as a result of incorporating one or more residues having side chains of particular interest at such location or locations in the analog upon which the investigation is focused. One such intermediate might include aminoglycine residues while another might include Aal or Asa or Mdg or Mda residues at the same positions.

In one aspect, the invention provides unnatural amino acids, termed "betidamino acids" which can be either L- or D-isomers or D/L mixtures and which are represented by the general formula:

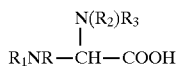

wherein $R_1$ is a labile alpha-amino-protecting group, R and $R_2$ are independently hydrogen or substituted or unsubstituted lower alkyl (preferably $C_1$ to $C_4$) wherein the alkyl substitution can be, for example, halo, hydroxy, amino, carboxy or the like, and $R_3$ is the remainder of an amino-reactive reagent, such as an acyl group, an isocyanate group, an isothiocyanate group, a sulfonyl group or the like.

In a broader aspect, the invention provides such betidamino acids, which can be either L- or D-isomers or D/L mixtures and which are represented by the general formula:

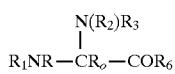

wherein $R_0$ is H or $CH_3$; R, $R_1$, $R_2$ and $R_3$ are as defined above; and $R_6$ is a labile protecting group or a blocking group for the carboxy function. Betides which include residues wherein R is $CH_3$ can be synthesized, for example, by using α-aminosarcosine (Asa) derivatives.

There are thousands of acyl groups or the like that can be incorporated in betides, examples of which include the products of reactions with substituted or unsubstituted, straight or branched chain carboxylic or heterocyclic carboxylic acids or their respective acyl halides, active esters, anhydrides and the like. Substitutions may be by groups such as chloro, bromo, fluoro, nitro, hydroxy, alkoxy, etc. One preferred subclass of betidamino acids includes those in which $R_3$ is an acyl group that resembles the side chain of a natural amino acid, in which $R_2$ is H or $CH_3$; and examples of such acyl groups include:

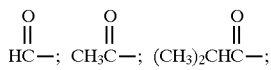

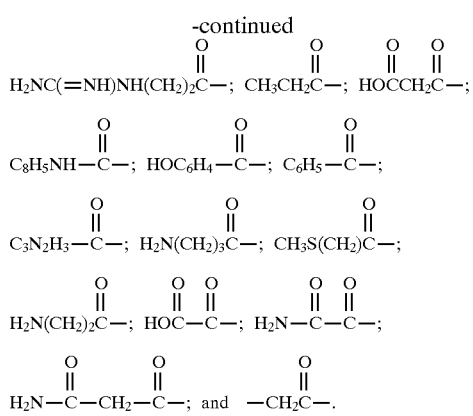

Another preferred subclass that is considered generally useful in synthesizing peptide analogs comprises betidamino acids wherein either $R_2$ or $R_2$ and $R_3$ together are selected to resemble fairly common amino derivatives or homologs. $R_2$ is H, $CH_3CH_2R_7$ or $CH_2CH_3$, where $R_7$ is OH, OMe, Cl, F, Br, I, $NH_2$, COOH, SH or an equivalent. $R_3$ is selected from the group which follows:

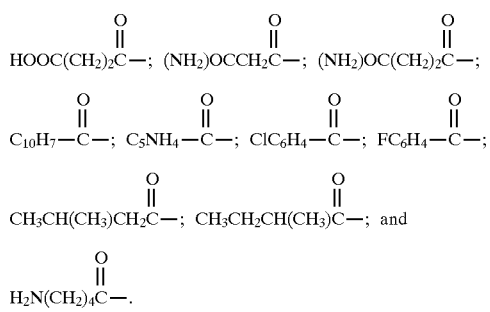

In another aspect, the present invention provides betides having at least one betidamino acid (as defined above), such betides having the formula:

$$X_N—X_1—X_2—X_3—X_m—X_4—X_5—X_6—X_C,$$

where $X_N$ is an acyl or other N-terminal group or a peptide up to about 50 amino acids in length having such an N-terminal group; $X_C$ is OH, $NH_2$ or other C-terminal group or a peptide up to about 50 amino acids in length having such a C-terminal group; $X_m$ is either des-X or a peptide up to about 50 amino acids, and $X_1$–$X_6$ are each independently des-X, a betidamino acid, a natural α-amino acid or an unnatural α-amino acid, provided however that at least one of $X_1$ to $X_6$ is a residue of a betidamino acid of the formula:

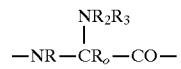

and that another of $X_1$ to $X_6$ is either a residue of a different betidamino acid of the formula:

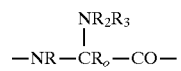

or an α-amino acid, wherein $R_0$, R, $R_2$ and $R_3$ are as defined above; and provided further however that additional residues of betidamino acids can optionally be included in $X_n$, $X_m$ and $X_c$.

In a further aspect, the invention provides a method for synthesizing betides which method comprises:
  a) providing a peptide intermediate having an amino acid residue with a free α-amino group at the N-terminus thereof,
  b) providing a protected betidamino acid precursor having the formula:

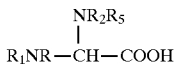

wherein $R_1$ and $R_5$ are labile amino-protecting groups independently removable under conditions that do not cause the removal of the other;
  c) coupling said precursor to the N-terminus of said intermediate to extend the length thereof by one residue;
  d) removing $R_1$ and coupling at least one alpha amino-protected amino acid or peptide thereto, or alternatively introducing an alkyl group at R and then coupling at least one alpha amino-protected amino acid or peptide thereto;
  e) removing $R_5$ from said intermediate to deprotect the amino group; and
  f) optionally modifying the deprotected amino group with an alkylating agent to introduce a lower alkyl moiety at $R_2$, and carrying out a reaction with an amino-reactive reagent such as a carboxylic acid, active ester or anhydride, an acyl halide, an isocyanate or isothiocyanate, a sulfonyl chloride or the like to cause an addition reaction to occur at the site of removal of $R_5$.

In a still further aspect, the invention provides a method for synthesizing betides which method comprises:
  a) providing a protected betidamino acid precursor having the formula:

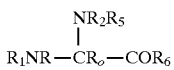

wherein $R_0$ is H or $CH_3$, $R_1$ and $R_5$ are labile amino-protecting groups independently removable under conditions that do not cause the removal of the other, R and $R_2$ are H or lower alkyl, and $R_6$ is a labile protecting group or a blocking group for the carboxy function;
  b) removing either $R_1$ or $R_6$ and coupling at least one appropriately protected amino acid or peptide thereto to create a peptide intermediate;
  c) removing $R_5$ from said intermediate to deprotect the amino group; and
  d) optionally modifying the deprotected amino group with an alkylating agent to introduce a lower alkyl moiety at $R_2$, and then carrying out a reaction with an amino-reactive reagent such as a carboxylic acid, active ester or anhydride, an acyl halide, an isocyanate or isothiocyanate, a sulfonyl chloride or the like to cause an addition reaction to occur at the site of removal of $R_5$. The α-carboxyl groups can be protected by suitable esters, e.g. benzyl and alkyl esters, as is well known in the art of classical solution synthesis, or can be blocked, as by amidation, when at the C-terminus of the desired betide.

The invention provides yet another method for making a desired betide by a chain elongation protocol, which method includes the steps of a) providing a resin or a peptide intermediate having an amino acid residue with a free α-amino group at the N-terminus thereof,
  b) providing an unnatural α-amino acid having the formula:

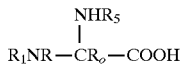

wherein $R_0$ is H or $CH_3$, R is H or lower alkyl, $R_1$ is a labile α-amino-protecting group, and $R_5$ is a labile amino-protecting group, $R_1$ and $R_5$ being respectively removable under conditions that do not cause the removal of the other;
  c) coupling said unnatural amino acid either to said resin or to said N-terminus of said intermediate;
  d) removing $R_1$ and coupling at least one α-amino protected amino acid or peptide thereto;
  e) removing $R_5$ from said intermediate; and
  f) providing an amino-reactive reagent such as a carboxylic acid, active ester or anhydride, an acyl halide, an isocyanate or isothiocyanate, a sulfonyl chloride or the like and causing an addition reaction to occur at the site of removal of $R_5$.

Presently preferred betides are those that are analogs of naturally occurring peptides. By way of example only, these betides may be analogs of somatostatin, vasopressin, angiotensin, thyrotropin releasing hormone(TRH), growth hormone releasing hormone (GRF), growth hormone releasing peptide (GRP), gonadotropin releasing hormone (GnRH), bradykinin, Substance P, bombesin, α-MSH, opioid peptides, and corticotropin releasing factor(CRF), containing at least one betidamino acid as described above, which betides have improved biopotency or are improved in some physical/chemical aspect as compared with corresponding native peptides or the like. Other preferred betides are those that are analogs of small active molecules such as aspartame (a peptide-based sugar substitute).

In still another aspect, the invention provides a pharmaceutical composition comprising a betide(s) of the invention in combination with a pharmaceutically acceptable excipient.

In yet a further aspect, the invention provides methods for easily and economically synthesizing betide libraries for use in screening betide analogs for biopotency or for another desired activity or property. Such screenings are useful for identifying desirable structures resulting from the use of betidamino acids which thereafter enables similar desirable structures to be incorporated in unnatural non-betidamino acids, if desired, for the subsequent synthesis of peptides that may have even further improved properties.

The invention further provides libraries of betides and methods for producing such libraries using the chain elongation protocol described just above wherein 1 or 2 or more residues of such unnatural α-amino acids having such formula are included in the chain. By using a plurality of aminoglycine residues in a single backbone, an even larger number of different betides can be created that will each have 2 or 3 or more residues of betidamino acids. For example, during a solid-phase synthesis, the beads of resin may be divided into 10 different portions and the side chain amino group of one aminoglycine residue is reacted with ten different acylating agents; then, recombining the beads, mixing them, then either adding another protected aminoglycine residue or separately deprotecting another aminoglycine residue in the chain, and repeating the acylation process with 10 different acylating agents after again dividing the group into 10 portions would produce 100 different intermediates because each of the 10 original intermediates would be turned into 10 new intermediates. By repeating the sequence a third time, either by coupling a third aminoglycine residue into the chain or by suitably sequentially deprotecting a third aminoglycine residue earlier incorporated within the chain, and then dividing the recombined group again into 10 portions and reacting with the 10 different acylating agents, the 100 intermediates are transformed into 1,000 different betides. Thus, the invention provides another way of creating a useful library of great diversity.

As one example of the foregoing, 2 or 3 such unnatural amino acids are coupled into the chain, each of which has a different labile $R_5$ protecting group, i.e. one may be base-labile, another thio-labile and the third may be hydrazine-labile. In such instance, the protecting groups are sequentially removed from the combined peptide-resin, e.g. first removing the base-labile group, the resin beads are divided into equal portions, and then each portion is reacted to carry out the acylation or the like addition reaction at the site of removal of $R_5$. The resin beads are then recombined, mixed and a second $R_5$ protecting group, e.g. the thio-labile group, is removed before division and reaction are again carried out. Subsequently, following recombination and removal of the hydrazine-labile protecting group, the final division and reaction takes place. When such a protocol is employed, each bead will contain precisely the same intermediate sequence. Therefore, by partially cleaving and deprotecting the betide from a particular bead and testing it for biological properties, if it should prove to have advantageous properties, it is possible to sequence the betide remaining on the bead of resin so as to determine the particular sequence of this member of the library that has been shown to be useful. Such partial cleavage is facilitated by connecting the C-terminal residue to the resin using two different linkers that can be orthogonally severed as is known in the art, e.g. one strong-acid-labile and one photo-labile.

Alternatively, instead of coupling 3 such diamino acids into the chain prior to the first of such side-chain reactions, one reaction can be carried out with the intermediate which contains only a single such residue, for example, by first removing a base-labile $R_5$ protecting group. Thereafter, the portions of the resin beads can be recombined before the chain elongation protocol is continued to couple into the chain a second such diamino residue again having a protecting group that is base-labile. Again, following removal of the protecting group and division, reaction is carried out at the site of the deprotected side chain amino group. Thereafter, the beads are again recombined, and further chain elongation takes place in a manner which can, if desired, include the coupling of still another such diamino amino acid, and then again repeating the foregoing side-chain reaction step. It can be seen that, using this strategy, 3 or even more such betidamino acids can be included, if desired, in a single chain thus multiplying the number of betides that will be present in the ultimate library.

Instead of using resin beads, plates or pins or wells containing a suitable resin for SPPS can be employed, in which instance individual reactions are carried out with each such pin or well or the like at each step. The result provides an automated synthesis of, for example, 96 different betides using a 96-well microtiter plate or the like. The strategy would be carried out in much the same way as explained hereinbefore except that each well would be treated with a different permutation of amino-reactive reagents so that, at the conclusion of the synthesis, 96 different betides would have been created, one in each of the wells. Because it was known as to what sequence of amino-reactive reagents was used in the betide-synthesis in each well, the composition of the particular betide in each well would be known so that, when subsequent testing shows a particular betide to be particularly biopotent, it would not be necessary to sequence the remaining betide because there would be a record of the sequence of residues making up that particular betide chain.

The betidamino acids can be prepared using processes described in the literature and generally known to those of skill in this art. For example, a particular betidamino acid according to the aforementioned formula can be prepared having a protecting group ($R_1$) on one amino group and having the desired side chain $NR_2R_3$ and such a protected betidamino acid can be coupled to a growing peptide chain in a conventional chain elongation peptide synthesis. Alternatively and preferably, a suitably protected aminoglycine or α-aminoalanine can be added at the desired position in the peptide chain during synthesis. Subsequently, the side chain amino group is deprotected, optionally alkylated, and then acylated. Deprotection, alkylation and acylation can be performed on the peptide intermediate or on the mature peptide, either while in solution, as in classical solution synthesis, or while attached to a resin as in SPPS. Acylation or other addition reaction is accomplished by reacting the deprotected amino group with an amino-reactive reagent, i.e. a carboxylic acid, active ester or anhydride, an acyl halide, e.g. chloride, an isocyanate or isothiocyanate, a sulfonyl chloride or the like. If a carboxylic acid is used, a standard coupling agent is included as well known in this art. Preferably, an acylating agent resembling the structure of the desired side chain is used. For example, reacting the deprotected alpha-aminoglycine residue with benzoyl chloride, under appropriate reaction conditions, results in formation of a betide residue having a side chain resembling that of Phe, and if first methylated, the residue will exhibit properties which generally mimic those of $C^\beta$-methyl-phenylalanine.

Appropriately protected aminoglycine (Agl) can be synthesized according to the method described by Brock, et al., *J. Org. Chem.* 51:3718 (1986) or by the method recently described by Qasmi, et al., *Tetrahedron Letters* 34(24):3861 (1993). In the latter article, there is described a strategy for making differentially protected aminoglycine, particularly suited for incorporation into a peptide via solid phase peptide synthesis (SPPS) using either a Boc or an Fmoc strategy. Alternative syntheses are disclosed in Schmidt, U. et al., *Synthesis,* 94, 890–892 (September 1994) for preparing differentially protected α-aminoglycines and their peptide derivatives. Differentially protected α-aminoalanine and α-aminosarcosine may be made by these methods or those disclosed in Simon et al., supra.

In preparing protected α-aminoglycine and incorporating the same into a peptide chain, it is preferred that one of the amino groups be protected in a manner that differs from protection employed for the other amino group, sometimes referred to as being orthogonally protected, so that either group can be selectively deprotected without affecting the other. An alternative is described hereinafter where only a single Boc group is removed from (bis-Boc) Agl. After completion of the entire α-aminoglycine-containing peptide chain (or at a desired intermediate length thereof, including immediately after coupling Agl), the side chain amino group of the α-aminoglycine residue is deprotected and selectively reacted to build the desired side chain group(s) at the position in the peptide chain where Agl was inserted.

As discussed in detail below, this method of preparing betides is particularly suited to synthesis of "betide libraries"

where a plurality of acylating agents is used to either independently or simultaneously create a plurality of different betides. Optionally, a plurality of alkylating agents may also be employed. Instead of incorporating aminoglycine into the peptide scaffold, Aal, Asa, Mdg or Mda can be used.

In the instance where it is desired to immediately build the side chain following coupling of the bis-protected aminoglycine to the peptide intermediate, then either of the two protecting groups on the respective amino groups can be removed for, at this point in the synthesis, the chain elongation process could take place from either one of these two groups. For instance, in a commonly used Boc strategy, Boc protection would be used on one of the amino groups and a suitable other protecting group would be used on the other amino group so that the other amino protecting group would not be removed under the mild acidic conditions used to remove Boc. The other protecting group can be one that is base-labile, e.g. Fmoc, thiol-labile, hydrazine-labile, photolabile or cleaved by reduction or the like. In such an instance, the Boc group may be removed first and then the chain can be extended or an alkylation and/or acylation reaction can be carried out to create the desired side chain.

If, for example, either the R or $R_2$ substituent in the betidamino acid is desired to be a methyl substituent, the primary amino group generated by removal of the Boc group may be temporarily alkylated with a removable group, such as by reaction with acid-sensitive 4,4'-dimethoxybenzhydryl chloride in the presence of triethylamine. Assuming $R_2$ is desirably methyl, this resulting secondary amino group can then be methylated by treatment with 36 weight percent aqueous formaldehyde, as a 30 volume percent solution with N-methylpyrrolidone (NMP) in the presence of excess cyanoborohydride. Thereafter, treatment with 60 percent TFA in DCM removes the dimethoxybenzhydryl group and produces a secondary amino group; reaction is then carried out by treatment with the desired acylating agent to create the di-substituted side chain amino group. The Fmoc protecting group is then removed to continue chain elongation. Alternatively, when simple acylation or reaction using another amino-reactive reagent, e.g. isocyanate, is being effected at the β-amino site, the Fmoc protection can be initially removed to provide the primary amino group which is immediately reacted to create the desired side chain; in such an instance, the Boc protection is subsequently removed to proceed with the chain elongation.

Betides can be synthesized by classical solution synthesis or, preferably, by a solid phase technique. In classical solution phase synthesis, addition may be made either to the N-terminus or the C-terminus of a growing chain, as well known in this art. When SPPS is used, elongation is preferably carried out at the N-terminus. A chloromethylated resin or a hydroxymethylated resin may be used, particularly when the C-terminus is free acid; however, when the peptide of interest has an amidated C-terminus, there is preferably employed a methylbenzhydrylamine(MBHA) resin, a benzhydrylamine (BHA) resin or some other suitable resin known in the art in order to directly provide a C-terminal amide or substituted amide upon cleavage. For example, peptides having a substituted amide at the C-terminus can be efficiently synthesized using an N-alkylamino methyl resin as taught in U.S. Pat. No. 4,569,967, issued Feb. 11, 1986.

Solid phase or other chain-elongation synthesis is conducted by stepwise addition of amino acids to the growing chain in the manner set forth in detail in the U.S. Pat. No. 4,211,693. Side-chain protecting groups are well known in the art and are preferably included as a part of any amino acid which has a particularly reactive side chain, for example His and b-His protected by tosyl; they are optionally included in the case of some other amino acids, such as Trp and b-Trp. When all the amino acids (including aminoglycine derivatives) have been coupled together in the chain being built upon the resin, a fully protected intermediate peptidoresin is obtained which can then be converted into a betidoresin by selectively deblocking the β-amino function and acylating the β-site amino group to add a synthesis-stable, acyl or other group. The aminoglycine (Agl) residue can be modified at this time to create a betide, or modification can be carried out at an earlier stage upon an intermediate peptidoresin of less than the full length, e.g. immediately after coupling Agl and before adding the next amino acid to the chain.

One example of an intermediate for making a betide analog of gonadotropin releasing hormone (GnRH) having a betidamino acid residue in the 2-position is represented by the formula: $X^1$-$AA_1$($X^2$)-Agl($X^3$)-$AA_3$($X^2$)-Ser($X^4$)-$AA_5$($X^5$)-D-$AA_6$-$AA_7$($X^2$ or $X^5$)-$AA_8$($X^6$ or $X^7$)-Pro-$X^8$ wherein the α-position residue provides a scaffold for a betidamino acid and wherein $AA_1$, $AA_3$, $AA_5$, D-$AA_6$, $AA_7$ and $AA_8$ are known amino acid residues that have been found to be effective in these respective positions. For example, described in U.S. Pat. No. 5,296,468 are various GnRH agonists and antagonists upon which such betide analogs may be based.

$X^1$ is an α-amino protecting or blocking group of the type known to be useful in the art in the stepwise synthesis of polypeptides. Among the classes of α-amino protecting groups are (1) aromatic urethane-type protecting groups, e.g., benzyloxycarbonyl(Z), fluorenylmethyloxycarbonyl (Fmoc) and substituted benzyloxycarbonyl, such as p-chlorobenzyloxy-carbonyl(ClZ), p-nitrobenzyloxycarbonyl, p-bromobenzyloxycarbonyl and p-methoxybenzyloxycarbonyl; (2) aliphatic urethane protecting groups, such as tertbutyloxycarbonyl(Boc), diisopropylmethoxycarbonyl, isopropyloxycarbonyl, ethoxycarbonyl and allyloxycarbonyl; (3) cycloalkyl urethan-type protecting groups, such as cyclopentyloxycarbonyl, adamantyloxycarbonyl and cyclohexyloxycarbonyl; (4) thiourethan-type protecting groups, such as phenylthiocarbonyl; (5) alkyl-type protecting groups, such as allyl(Aly), triphenylmethyl(trityl) and benzyl(Bzl); (6) trialkylsilane groups, such as trimethylsilane. The preferred α-amino protecting groups are Boc and Fmoc. Also among the classes of α-amino blocking groups which might be employed for the residue at the N-terminus of the desired betide are the acyl-type groups, such as acetyl (Ac), formyl(For), trifluoroacetyl, acrylyl(Acr), chloroacetyl and the like, with Ac being preferred.

$X^2$ is hydrogen or a protecting group for the indole nitrogen of Trp, such as Bz, Ac or For. In many syntheses there is no need to protect Trp, but if protection is desired, formyl is preferred.

$X^3$ is a protecting group for the side chain amino group of Agl or Aal or the like which is not removed when the α-amino protecting group is removed. Illustrative examples include (1) base-labile groups, such as Fmoc, or some other weak-acid stable, aromatic urethane-type protecting group; (2) thiol-labile groups, such as dithiasuccinoyl(Dts) which may be removed or cleaved by thiolysis; (3) hydrazine-labile groups, such as phthaloyl(Pht) which is cleaved by hydrazinolysis; (4) nucleophile-labile groups, such as o-nitrophenylsulfenyl(Nps) and the like which are cleaved by thioacetamide or by weak acids or their salts; (5) photolabile groups which are cleaved by photolysis; and (6) groups selectively removable by reduction, such as Dts.

Fmoc is preferred for a Boc SPPS strategy. $X^3$ can also be an acyl group that constitutes the ultimate side chain of the desired betidamino acid. Depending on the nature of the acyl group, additional protection may be required for this group.

$X^4$ is hydrogen or a protecting group for the hydroxyl side chain of Ser, e.g. Ac, Bz, trityl, DCB or benzyl ether(Bzl) and is preferably Bzl.

$X^5$ is hydrogen or a protecting group for the phenolic hydroxyl group of Tyr selected from the group consisting of tetrahydropyranyl, tert-butyl, trityl, benzyl, Z, 2-bromobenzyloxycarbonyl(2BrZ) and 2,6-dichlorobenzyl (DCB). 2BrZ is preferred.

$X^6$ is a protecting group for a side chain guanidino group in Arg or Har, such as Boc, nitro, Tos, trityl, adamantyloxycarbonyl, Z and 2,4-dinitrophenol(Dnp), or $X^6$ may be hydrogen, which means there is no protection on the side chain group atoms. Tos is generally preferred.

$X^7$ is a protecting group for either a primary or secondary amino side chain group, such as Z or 2ClZ.

$X^8$ may be Gly-NH-[resin support], D-Ala-NH-[resin support] or N(A)-[resin support]; $X^8$ may also be an amide either of Gly or of D-Ala, or a substituted amide attached directly to Pro, NHNHCONH$_2$ or the like.

When the $X^8$ group is Gly-NH-[resin support] or D-Ala-NH-[resin support], an amide bond connects Gly or D-Ala to a BHA resin or to a MBHA resin. When the $X^8$ group is N(A)-[resin support], a substituted amide bond connects Pro to an N-alkylaminomethyl (NAAM) resin. When $X^8$ is AzaGly-NH$_2$, the peptide is preferably made by classical solution synthesis, as disclosed in U.S. Pat. No. 4,234,571.

The selection of suitable protecting groups is well within the skill of those working in the art to which the invention pertains. Further information regarding the selection of suitable protecting groups is available in Barany, G.; Kneib-Cordonier, N.; Mullen, D. G. "Solid-phase peptide synthesis: a Silver Anniversary report," *Intl. J. Prot. Pep. Res.* 1987, 30, 705–739; and in Barany, G. and Merrifield, R. B. "Solid-phase peptide synthesis", in *The Peptides, Analysis, Synthesis, Biology;* Gross, E., Meienhofer, J., Eds., Academic Press, New York, 1980; V. 2, pp 1–284.

The criterion for selecting certain of the side chain protecting groups for $X^2$–$X^7$ is that the protecting group should be stable to the reagent under the reaction conditions selected for removing the α-amino protecting group (preferably Boc) at each step of the synthesis. These protecting groups generally should not be split off under coupling conditions but should be removable upon completion of the synthesis of the desired amino acid sequence under reaction conditions that will not alter the peptide chain. Other protecting groups employed for the Agl residue, which may also be employed for certain 5- and/or 6-position residues in GnRH antagonists, are removed prior to cleavage from the resin, as explained hereinafter, in order to permit subsequent reactions that are effected to build the desired final residues at these positions.

Thus, for example, in one fairly specific aspect, the invention also provides a method for making a GnRH antagonist having the formula: Ac-β-D-2NAL-(4Cl)D-Phe-AA$_3$-Ser-Aph(Ac)-D-Aph(Ac)-Leu-ILys-Pro-D-Ala-NH$_2$, wherein AA$_3$ is a residue of a betidamino acid as set forth hereinbefore, which method comprises (a) forming an intermediate peptide having the formula: $X^1$-β-D-2NAL-(4Cl) D-Phe-Agl($X^3$)-Ser($X^4$)-Aph(Ac)-D-Aph (Ac)-Leu-ILys ($X^7$)-Pro-D-Ala-NH-[resin support], wherein $X^1$ is hydrogen or an α-amino protecting group; $X^3$ is an amino protecting group that is removable without removing other protecting groups; $X^4$ is a protecting group for a hydroxyl group of Ser; and $X^7$ is a protecting group for an amino side chain; (b) removing $X^1$ and acylating the N-terminus; (c) removing $X^3$ from Agl to deprotect the side chain amino group thereof in said intermediate peptide; (d) reacting said deprotected side chain amino group to build this residue into one having the desired β-site modification; and (e) splitting off any remaining protecting groups and/or cleaving from the resin support included in $X^8$.

Purification of the betide is effected by known procedures, such as ion exchange chromatography on a CMC column, followed by partition chromatography using a suitable elution system, e.g. n-butanol:0.1N acetic acid (1:1 volume ratio) on a column packed with Sephadex G-25, and/or by using HPLC, as known in the art and specifically set forth in J. Rivier, et al. *J. Chromatography,* 288 (1984) 303–328. GnRH antagonists such as these are effective at levels of less than 100 micrograms per kilogram of body weight, when administered subcutaneously at about noon on the day of proestrus, to prevent ovulation in female rats. For prolonged suppression of ovulation, it may be necessary to use dosage levels in the range of from about 0.001 to about 2.5 milligrams or more per kilogram of body weight per day. Such GnRH antagonists are also effective to arrest spermatogenesis when administered to male mammals on a regular basis and can thus be used as male contraceptives. Since these compounds will reduce testosterone levels (an undesired consequence in the normal, sexually active male), it may be desirable to administer replacement dosages of testosterone along with the GnRH antagonist. These antagonists can also be used to regulate the production of gonadotropins and sex steroids for other purposes as generally known in this art.

Betides provided by the invention, relative to the corresponding non-betide peptides, are particularly soluble at physiological pHs. Thus, the betides of the invention can be prepared as relatively concentrated solutions for administration, particularly for subcutaneous injection. These betides are well-tolerated in the body and exhibit a lesser tendency to gel and remain at the point of injection than the counterpart non-betide peptides when administered subcutaneously. Generally pharmaceutical compositions including such betides and a suitable pharmaceutically acceptable excipient can be administered iv, ip, subcutaneously or the like at levels of between about 0.001 mg to about 2.5 mgs per Kg of body weight per day.

Although the appropriately protected betidamino acid can be synthesized and then employed in a chain elongation peptide synthesis, synthesis of an analog of a potentially biopotent peptide having an α-aminoglycine incorporated at a particular location of interest is preferably used. Moreover, such a strategy is advantageously employed as a first step in determining prospective biopotency of peptide analogs substituted with a variety of different substituents at one position in the peptide by creating a "library" of such analogs that will be the same except for the side chain of the residue at the selected position. This strategy is accomplished by reacting the deprotected side chain amino group of the α-aminoglycine residue with what can be a plurality of reactants which will create a plurality of betides having the desired side chains of interest, using one of the methods hereinbefore described.

One preferred method of preparing a library using solid-phase synthesis is carried out wherein a peptide scaffold is established wherein 1, 2, 3 or more aminoglycine or equivalent residues are incorporated within the backbone of the peptide chain. These residues are then individually selectively deprotected, and reaction is carried out using one of the aforedescribed strategies: either dividing resin beads into individual portions for separate reactions with a single reactant and then recombining the beads, mixing them and repeating the selective deprotection and reaction steps, or using separate pins, plates or wells and programming the successive reactions. Using such a bead strategy, if one reacts with 10 reactants each time, and there are 3 residues that are sequentially so reacted, one obtains 10×10×10, or 1,000 different betide products. Most importantly, each of the betides on a single resin bead will have the same sequence so that, if that betide is found to have advantageous properties when tested, its precise formula can be determined by sequence analysis of the remaining material. When individual pins or wells are used, the sequence of the particular betide in each well is known.

An alternative strategy is to carry out the acylation reaction using a mixture of acylating agents as hereinbefore described. This strategy allows one to simultaneously synthesize a betide mixture to test the effect on biopotency of various amino acid residue substitutions at one location; the test results will show whether any betide in the mixture having one of the multiple substitutions exhibits improved biopotency. If improved biopotency is discovered when testing the mixture, the particular side chain or side chains so responsible are later determined via the process of elimination.

In many of the following formulas for GnRH antagonists, the residues which appear in positions 5 and 6 are sometimes defined in terms of the original amino acid residue having a side chain amino group, e.g. p-aminophenylalanine (Aph), plus a modification to the para-amino group which is set forth in the accompanying parentheses. The Agl residues are often similarly represented. Preferably, the original unmodified residue is incorporated in the main peptide chain, for example, Aph or the respective D-isomer thereof or D/L Agl, and is later modified while a part of the peptide chain that is still attached to the resin. Such a modification of Aph or the like is appropriately coordinated with the modification of Agl or the like; it may take place separately, either before or after the modification to create the betide, or simultaneously therewith if the same modification, e.g. acylation, is being made to all such residues. However, a suitably protected betidamino acid can alternatively be added to the growing peptide chain as a part of the usual chain elongation process, if desired.

The present invention is further described by the examples which follow. Such examples, however, are not to be construed as limiting in any way either the spirit or the scope of the present invention. Some of the following examples illustrate GnRH antagonist and somatostatin agonist betides embodying various features of the invention. All of these particular betides include at least one D-isomer amino acid residue.

EXAMPLE 1

The peptide having the formula: Ac-β-D-2NAL-(4Cl)D-Phe-D-3PAL-Ser-Aph(Ac)D-Aph(Ac)-Leu-ILys-Pro-D-Ala-NH$_2$ has been found to exhibit very good biological properties as a GnRH antagonist and is generally referred to as Acyline. It is therefore desirable to make betides patterned after this decapeptide having one or more betidamino acids in the sequence.

The following decabetide [Ac-β-D-2NAL$^1$, (4Cl)D-Phe$^2$, D/L Agl(nicotinoyl)$^3$, Aph(Ac)$^5$, D-Aph(Ac)$^6$, ILys$^8$, D-Ala$^{10}$]-GnRH (Betide No. 1) is synthesized by solid-phase synthesis. This betide has the following formula: Ac-β-D-2NAL-(4Cl)D/L-Phe-γ-(3-pyridyl)amidoGly-Ser-Aph (acetyl)-D-Aph(acetyl)-Leu-Lys(isopropyl)-Pro-D-Ala-NH$_2$.

About 3 grams (0.76 mM/g) of MBHA resin are initially used, and Boc-protected D-Ala is coupled to the resin over about a 100 minute period in N-methylpyrrolidone(NMP)/CH$_2$CL$_2$ using about 5 millimoles of Boc derivative and diisopropylcarbodiimide (DIC) as an activating or coupling reagent. The D-Ala residue attaches to the MBHA residue by an amide bond.

Following the coupling of each amino acid residue, washing, deblocking and coupling of the next amino acid residue is carried out in accordance with the following schedule using an automated machine, which schedule may be used for a synthesis being carried out upon about 3 grams of resin:

| STEP | REAGENTS AND OPERATIONS | MIX TIMES MIN. |
|---|---|---|
| 1 | CH$_2$Cl$_2$wash—80 ml. (2 times) | 1 |
| 2 | Methanol (MeOH) wash—30 ml. (2 times) | 1 |
| 3 | CH$_2$Cl$_2$ wash—80 ml. (3 times) | 1 |
| 4 | 50% TFA plus 5% 1,2 ethanedithiol in CH$_2$Cl$_2$—70 ml. (2 times) | 15 |
| 5 | Isopropyl alcohol + 1% ethanedithiol wash—80 ml. (2 times) | 1 |
| 6 | TEA 12.5% in CH$_2$Cl$_2$—70 ml. | 1 |
| 7 | MeOH wash—40 ml. (2 times) | 1 |
| 8 | TEA 12.5% in CH$_2$Cl$_2$—70 ml. (2 times) | 1 |
| 9 | CH$_2$Cl$_2$ wash—80 ml. (3 times) | 1 |
| 10 | Boc-amino acid (5 mmoles) in 30 ml. of CH$_2$Cl$_2$ (DCM) or dimethylformamide(DMF): DCM or NMP:DCM, depending upon the solubility of the particular protected amino acid, plus DIC or DCC (5 mmoles) in CH$_2$Cl$_2$ | 90–120 |
| 11 | MeOH wash—40 ml. (2 times) | 1 |
| 12 | Triethylamine(TEA) 12.5% in CH$_2$Cl$_2$—70 ml. | 1 |
| 13 | MeOH wash—30 ml. (2 times) | 1 |
| 14 | DCM wash—80 ml. (2 times) | 1 |

The above schedule is used for coupling of each of the amino acids of the peptide of the invention after the first amino acid has been attached. N$^\alpha$Boc protection is used for each of the amino acids coupled throughout the synthesis. N$^\alpha$Boc-β-D-2NAL is prepared by a method known in the art, e.g. as described in detail in U.S. Pat. No. 4,234,571, issued Nov. 18, 1980; it is also commercially available from SyntheTech, Oregon, U.S.A. The side chain primary amino groups of Aph in the 5-position and of D-Aph in the 6-position are protected by Fmoc. Benzyl ether (Bzl) is preferably used as a side chain protecting group for the hydroxyl group of Ser; however, Ser may be coupled without side chain protection. Boc-Lys(Ipr,Z) is used for the 8-position residue.

After adding Ser for the 4-position residue as N$^\alpha$Boc-Ser (Bzl), the following intermediate is present: Boc-Ser(Bzl)-Aph(Fmoc)-D-Aph(Fmoc)-Leu-Lys(Ipr,Z)-Pro-D-Ala-NH-[MBHA resin support]. The side chains on the amino acid residues in the 5- and 6-positions are then modified by simultaneously acetylating them after first removing the side-chain protection. The Fmoc protecting group is removed from both residues by treatment with 20 percent piperidine in DMF (10 ml) for about 30 minutes; the intermediate is preferably washed with DMF and then treated with more piperidine/DMF for another 30 minutes. After preferably washing the peptidoresin with DMF, the newly freed amino groups are treated with a large excess of acetic anhydride in DCM for 15 minutes or until complete as checked using a ninhydrin test, at room temperature to acetylate both side chains. The peptide resin is then subjected to the standard wash.

Following completion of the acetylation of the Aph residues, Boc and Fmoc-protected D/L-aminoglycine is coupled to the chain for the residue in the 3-position. Once added, the Boc protection is removed, the subsequent residue is added, and the completion of the chain is carried out. After deblocking the α-amino group at the N-terminus using trifluoroacetic acid (TFA), acetylation is achieved using a large excess of acetic anhydride in dichloromethane.

After acetylation of the N-terminus, the Agl side chain is selectively deprotected and acylated with nicotinic acid in DCM for 4 hours to form the γ-3-pyridylamidoglycine residue using an appropriate coupling agent such as DCC and create what is referred to as a betide intermediate.

The betidoresin is dried, and then cleavage of the betide from the resin and deprotection of the Ser and the Lys side chains are carried out at 0° C. with HF for about 40 min. Anisole is added as a scavenger prior to HF treatment. After the removal of HF under vacuum, the resin is washed twice with 100 ml. of ethyl ether. The cleaved betide is extracted from the resin with equal parts of $CH_3CN$ and $H_2O$, repeating the process and using 100 ml. each time. The extracts are pooled and lyophilized, and they provide a crude betide powder.

Purification of the betide is then effected by preparative high performance liquid chromatography (HPLC), as known in the art and specifically set forth in J. Rivier, et al. *J. Chromatography*, 288, 303–328 (1984). The first preparative RP-HPLC separation uses a TEAP (triethylammonium phosphate) buffer system. This separation is repeated using the same buffer system with a slightly different gradient, and a final separation is carried out using a 0.1% TFA (trifluoroacetic acid) gradient, all as described in detail in the *J. Chromatography* article. The two betides having the L- and D-isomers of Agl at position 3 are therefore separated and desalted using this procedure.

The betide fractions are judged to be homogeneous using capillary zone electrophoresis (CZE), as well as by using reversed-phase high performance liquid chromatography (RP-HPLC) and an aqueous triethylammonium phosphate buffer plus acetonitrile. The purity is estimated to be about 97%–98%. Amino acid analysis of the resultant, purified betide is consistent with the formula for the prepared structure, showing substantially integer-values for each amino acid in the chain; liquid secondary ion mass spectrometry (LSIMS) is also consistent. The optical rotation is measured on a photoelectric polarimeter as $[\alpha]_D^{20}=-34.0°$ and $-24.4°\pm1$ (c=1, 50% acetic acid) for the two stereoisomers, isomers (1) and (2). LSIMS analysis showed the expected mass of 1561.8 Da for both isomers.

The betide is assayed in vivo to determine its effectiveness to prevent ovulation in female rats. In this test, a specified number of mature female Sprague-Dawley rats, e.g. five to ten, each having a body weight from 225 to 250 grams, are injected with a specified microgram dosage of the betide in bacteriostatic water at about noon on the day of proestrus. Proestrus is the afternoon of ovulation. A separate female rat group is used as a control to which the peptide is not administered. Each of the control female rats ovulates on the evening of proestrus; the number of the rats treated which ovulate is recorded. In vivo testing of the two isomeric betides shows that, at a dosage of 2.5 microgram, 0 out of 7 and 0 out of 5 rats treated ovulate for isomers (1) and (2), respectively. At a dosage of 1.0 microgram for isomer (1), all ovulate while for 1 µg of isomer (2), only 6 out of 14 rats ovulate and for 0.5 µg, 3 out of 4 rats ovulate. Isomer (2) is hereinafter referred to as Betide No. 1. Examination of the rats shows that the betide was very well tolerated, with no significant gelling at the point of injection being detectable.

Hydrophilicity is tested by measuring retention using RP-HPLC with a gradient of 40% Buffer B to 75% Buffer B over 30 minutes, with Buffer A being TEAP pH 7.3 and Buffer B being 60% $CH_3CN$ and 40% Buffer A. Betide No. 1 is more hydrophilic, eluting at 23.5 minutes compared to 24.1 minutes for Acyline. The betide is considered to be particularly useful because of its solubility in aqueous buffers at a pH of from about 5 to about 7 and its resistance to invivo gelling, which renders it particularly suitable for administration by subcutaneous injection compared to other compounds of generally comparable biological efficacy. Moreover, Betide No. 1 exhibits fairly long-acting biopotency, suppressing circulating LH concentrations to levels that are less than 25% of control levels for 48 hours or more at a dose of 50 micrograms per rat.

EXAMPLE 1A

The synthesis set forth in Example 1 is repeated, substituting isonicotinoyl chloride in DCM and reacting for 4 hours to form the 4-pyridylamidoglycine residue. Cleavage from the resin and deprotection, followed by purification, are carried out as described n Example 1. The betide Ac-β-D-2NAL-(4Cl)D-Phe-γ-(4-pyridyl) D/L-amidoGly-Ser-Aph(acetyl)-D-Aph(acetyl)-Leu-Lys(isopropyl)-Pro-D-Ala-$NH_2$ (Betide No. 1A) is judged to be homogenous, and the purity is estimated to be greater than 80 percent. The optical rotation is measured on a photoelectric polarimeter as $[\alpha]_D^{20}=-31.5°$ and 25.4°, ±1 (c=1, 50% acetic acid) respectively for the two isomers. MS analysis showed the expected mass of 1561.8 Da for both isomers. Both of these betides are also more hydrophilic than Acyline.

Assaying these two betides in the standard invivo rat anti-ovulation test shows that, at dosages of 10 micrograms, 3 out of 7 and 0 out of 8 rats respectively ovulate; at a dosage of 2.5 micrograms, only the second isomer was bioactive, with 2 out of 8 rats ovulating.

EXAMPLE 2

The betide having the formula Ac-β-D-2NAL-(4Cl)D-Phe-D-3PAL-Ser-Aph(acetyl)-D-Aph (acetyl)-D/LAgl (Acetyl)-Lys(Isopropyl)-Pro-D-Ala-$NH_2$ (Betide No. 2) is synthesized using the synthesis as set forth in Example 1. Instead of coupling $N^\alpha$Boc-D/L-Agl(Fmoc) in the 3-position, it is coupled in the 7-position, as a precursor to Agl(acetyl), and D-3PAL is coupled in the 3-position. In this synthesis, following the coupling of the first 6 residues, the following peptide intermediate is obtained: Boc-Aph(Fmoc)-D-Aph(Fmoc)-D/L-Agl(Fmoc)-Lys(Ipr,Z)-Pro-D-Ala-NH-[MBHA resin support]. The side chains on the Aph residue, the D-Aph residue and the Agl residue are then simultaneously deprotected by removal of the Fmoc protection using 20 percent piperidine in DMF (10 ml) for about 30 minutes. After washing with DMF, the piperidine/DMF treatment is repeated. After a final wash with DMF, the intermediate is treated with a large excess of acetic anhydride in DCM for about 10 minutes at room temperature to simultaneously acetylate the side chains of these 3 residues.

The betidoresin is then subjected to the standard wash, and the synthesis is completed using the method as generally taught in Example 1.

Cleavage from the resin and deprotection, followed by purification, are carried out as described in Example 1. The betide Ac-β-D-2NAL-(4Cl)D-Phe-D-(3-pyridyl)Ala-Ser-Aph(acetyl)-D-Aph(acetyl)-D/L-Agl(Acetyl)-Lys (isopropyl)-Pro-D-Ala-NH$_2$ (Betide No. 2) is judged to be homogeneous, and the purity is estimated to be greater than 80 percent. The optical rotation of the mixture is measured on a photoelectric polarimeter as $[\alpha]_D^{20}$=−18.1°±1 (c=1, 50% acetic acid) It is a mixture of two isomers respectively having D- and L-Agl(Ac) at position 7. MS analysis shows the expected mass of 1534.7 Da for the mixture. RP-HPLC shows that the mixture is more hydrophilic than Acyline.

Assaying the betide mixture using the standard in vivo rat anti-ovulation test shows that, at a dosage of 10 micrograms, 0 out of 8 rats ovulate and at a dosage of 5 micrograms, 5 out of 8 rats ovulate. 10 micrograms, 0 out of 8 rats ovulate and at a dosage of 5 micrograms, 5 out of 8 rats ovulate.

EXAMPLE 3A

The betide having the formula Ac-D/L-Agl(2-naphthoyl)-D-4Cpa-D-3PAL-Ser-Aph(acetyl)-D-Aph (acetyl)-Leu-Lys(isopropyl)-Pro-D-Ala-NH$_2$ is synthesized using the synthesis as set forth in Example 1. Instead of coupling N$^\alpha$Boc-D/L-Agl(Fmoc) in the 3-position, it is coupled in the 1-position following acetylation of the Aph and D-Aph side chains. D-3PAL is coupled in the 3-position. In this synthesis, following the completion of the decapeptide and the acetylation of the N-terminus, the following peptide intermediate is obtained: Ac-D/L-Agl(Fmoc)-4Cl-D-Phe-D-3PAL-Ser(Bzl)-Aph(Ac)-D-Aph (Ac)-Leu-Lys(Ipr,Z)-Pro-D-Ala-NH-[MBHA resin support]. The side chain on the Agl residue is then deprotected by removal of the Fmoc protection using 20 percent piperidine in DMF (10 ml) for about 30 minutes. After washing with DMF, the piperidine/DMF treatment is repeated. After a final wash with DMF, the intermediate is treated with 10 millimoles of 2-naphthoyl chloride in a mixture of equal parts of DMF and DCM in the presence of a tertiary amine, i.e. diisopropylethylamine (DIPEA), for about 20 minutes at room temperature to acylate the side chain of the Agl residue.

The betidoresin is then subjected to the standard wash, and cleavage from the resin and deprotection, followed by purification using two different buffer systems, are carried out as described in Example 1. The betide Ac-γ-(2-naphthoyl)amidoGly-4Cl-D-Phe-D-3PAL-Ser-Aph(acetyl)-D-Aph(acetyl)-Leu-Lys (isopropyl)-Pro-D-Ala-NH$_2$ (Betide No. 3A) is judged to be homogeneous, and the purity is estimated to be greater than 90 percent. The two stereoisomers are separated in the RP-HPLC purification, and the optical rotations are measured on a photoelectric polarimeter as $[\alpha]_D^{20}$=−31.0° and −1.2°±1 (c=1, 50% acetic acid) respectively, for the two isomers. MS analysis shows the expected mass of 1561.8 Da for both isomers.

Assaying the betides using the standard in vivo rat ovulation test shows that the second isomer is fully active (0/8) at 5 μg, and the first isomer is fully active (0/8) at 2.5 μg. The second isomer is inactive (5/5) at 2.5 μg, but the first isomer is active at a dosage of 1 μg, i.e., only 2 out of 4 rats ovulate (7 eggs total).

EXAMPLE 3B

The betide similar to that synthesized in Example 3A is made, which has the formula Ac-D/L-Agl(2-naphthoyl)-D-4Cpa-D-3PAL-Ser-Aph(atz)-D-Aph(atz)-Leu-Lys(isopropyl)-Pro-D-Ala-NH$_2$. The synthesis set forth in Example 3A is used, but the Aph and D-Aph side chains, instead of being acetylated, are reacted to form the 3-amino amino 1,2,4 triazole moieties as in Example 3. In this synthesis, following the completion of the decapeptide and the acetylation of the N-terminus, the following peptide intermediate is obtained: Ac-D/L-Agl(Fmoc)-4Cl-D-Phe-D-3PAL-Ser(Bzl)-Aph(atz)-D-Aph (atz)-Leu-Lys(Ipr,Z)-Pro-D-Ala-NH-[MBHA resin support]. The side chain on the Agl residue in the 1-position is then deprotected by removal of the Fmoc protection using 20 percent piperidine in DMF (10 ml) for about 30 minutes. After washing with DMF, the piperidine/DMF treatment is repeated. After a final wash with DMF, the intermediate is treated with 10 millimoles of 2-naphthoyl chloride in a mixture of equal parts of DMF and DCM in the presence of a tertiary amine, i.e. diisopropylethylamine (DIPEA), for about 20 minutes at room temperature to acylate the side chain of the Agl residue.

The betidoresin is then subjected to the standard wash, and cleavage from the resin and deprotection, followed by purification using two different buffer systems, are carried out as described in Example 1. The betide Ac-γ-(2-naphthoyl)amidoGly-4Cl-D-Phe-D-3PAL-Ser-Aph(atz)-D-Aph(atz)-Leu-Lys(isopropyl)-Pro-D-Ala-NH$_2$ (Betide No. 3B) is judged to be homogeneous, and the purity is estimated to be greater than 90 percent. The two stereoisomers are separated in the RP-HPLC purification, and the optical rotations are measured on a photoelectric polarimeter as $[\alpha]_D^{20}$=−23.0° and −2.0°±1 (c=1, 50% acetic acid) respectively, for the two isomers. MS analysis shows the expected mass of 1642.0 Da for both isomers.

Assaying the betides using the standard in vivo rat ovulation test shows that the first isomer is fully active (0/8) at 2.5 μg. The second isomer is fully active (0/3) at 2.5 μg, and at a dosage of 1 μg for the second isomer, 4 out of 8 rats ovulate.

EXAMPLE 4

The betide having the formula: Ac-β-D-2NAL-(4Cl)D-Phe-D-3PAL-Ser-(4-Acetyl-amino-benzyl)D/L-amidoGly-D-Aph(acetyl)-Leu-Lys(isopropyl)-Pro-D-Ala-NH$_2$ is synthesized using the synthesis as set forth in Example 1. Instead of coupling N$^\alpha$Boc-D/L-Agl(Fmoc) in the 3-position, it is coupled in the 5-position, following acetylation of the D-Aph side chain. Ser is coupled in the 4-position, and the remainder of the chain completed. In this synthesis, following the completion of the decapeptide and the acetylation of the N-terminus, the following peptide intermediate is obtained: Ac-β-D-2NAL-(4Cl)D-Phe-D-3PAL-Ser(Bzl)-D/L-Agl(Fmoc)-D-Aph(Ac)-Leu-Lys(Ipr,Z)-Pro-D-Ala-NH-[MBHA resin support]. The side chain on the Agl residue is deprotected by removal of the Fmoc protection using 20 percent piperidine in DMF (10 ml) for about 30 minutes. After washing with DMF, the piperidine/DMF treatment is repeated. After a final wash with DMF, the intermediate is treated with 2 millimoles of acetyl-para-aminobenzoic acid (Ac-Paba) in DMF in the presence of HBTU for about 30 to 60 minutes at room temperature to acylate the side chain of the Agl residue.

The betidoresin is then subjected to the standard wash, and cleavage from the resin and deprotection, followed by purification, are carried out as described in Example 1. The resulting betide Ac-β-D-2NAL-(4Cl)D-Phe-D-3PAL-Ser-(4-Acetyl-amino-benzyl)D/L-amidoGly-D-Aph(acetyl)-Leu-Lys(isopropyl)-Pro-D-Ala-NH$_2$ (Betide No. 4) is judged to be homogeneous, and the purity is estimated to be greater than 80 percent. The optical rotation of the mixture is measured on a photoelectric polarimeter as $[\alpha]_D^{20}$=−18.9°±1 (c=1, 50% acetic acid) for the mixture of the two isomers. MS analysis shows the expected mass of 1561.8 Da.

Assaying the betide mixture using the standard in vivo rat ovulation test shows that, at a dosage of 5 micrograms, 2 out of 8 rats ovulate.

EXAMPLE 4A

The synthesis set forth in Example 4 is repeated, substituting 4-hydroxybenzoic acid in DMF/DCM for 4-Acetylaminobenzoic acid and reacting for 7 hours in the presence of DIC and 1-hydroxybenzotriazole to form the (4-hydroxyphenyl)amidoglycine residue. Cleavage from the resin and deprotection, followed by purification, are carried out as described in Example 1. The betide Ac-β-D-2NAL-(4Cl)D-Phe-D-3PAL-Ser-γ-(4-hydroxyphenyl)D/L-amidoGly-D-Aph(acetyl)-Leu-Lys(isopropyl)-Pro-D-Ala-NH$_2$ (Betide No. 4A) is judged to be homogeneous, and the purity is estimated to be greater than 80 percent. The optical rotation is measured on a photoelectric polarimeter as $[\alpha]_D^{22}$=−20.0°±1 (c=1, 50% acetic acid) for the mixture of the two isomers. MS analysis shows the expected mass of 1521.8 Da.

Assaying the betide mixture using the standard in vivo rat anti-ovulation test shows that, at a dosage of 5 micrograms, 2 out of 16 rats ovulate.

EXAMPLE 5

The betide having the formula Ac-β-D-2NAL-(4Cl)D-Phe-D-3PAL-Ser-Aph(acetyl)-γ-(4-acetamidophenyl)D/L-amidoGly-Leu-Lys(isopropyl)-Pro-D-Ala-NH$_2$ is synthesized using the synthesis as set forth in Example 1. Instead of coupling N$^\alpha$Boc-D/L-Agl(Fmoc) in the 3-position, it is coupled in the 6-position, and D-3PAL is coupled in the 3 position. Immediately following the coupling of Agl, the Fmoc group is removed, and a reaction is carried out with Paba(Fmoc) as generally described in Example 4. Following a wash with DCM, Boc is removed, and N$^\alpha$Boc-Aph(Fmoc) is next coupled to create the following betide intermediate: Boc-Aph(Fmoc)-D/L-Agl (aminobenzyl)(Fmoc)-Leu-Lys(Ipr,Z)-Pro-D-Ala-NH-[MBHA resin support]. The side chains on both the Agl and Aph residues are then simultaneously deprotected by removal of the Fmoc protection using 20 percent piperidine in DMF (10 ml) for about 30 minutes. After washing with DMF, the piperidine/DMF treatment is repeated. After a final wash with DMF, the intermediate is treated with a large excess of acetic anhydride in DCM for about 10 minutes at room temperature to simultaneously acetylate the side chains of both these residues. The completion of the synthesis is then carried out by adding the remaining 4 amino acids and acetylating the N-terminus as in Example 4.

The betide resin is then subjected to the standard wash, and cleavage from the resin, deprotection, and purification are carried out as described in Example 1. The resulting betide Ac-β-D-2NAL-(4Cl)D-Phe-D-3PAL-Ser-Aph(acetyl)-γ-(4-acetamidophenyl)D/L-amidoGly-Leu-Lys(isopropyl)-Pro-D-Ala-NH$_2$ (Betide No. 5) is judged to be homogenous, and the purity is estimated to be greater than 80 percent. The optical rotation is measured on a photoelectric polarimeter as $[\alpha]_D^{22}$=−27.5°±1 (c=1, 50% acetic acid) as a mixture of the two isomers. MS analysis shows the expected mass of 1561.8 Da for both isomers.

Assaying the peptide with the standard in vivo rat ovulation test shows that, at a dosage of 5.0 micrograms, 1 out of 8 rats ovulate and at a dosage of 2.5 microgram, 2 out of 4 rats ovulate.

The foregoing betides tested exhibit biological potency, from the standpoint of antiovulatory effect, which is generally comparable to the parent peptide of which each is an analog. Based upon superior solubility, resistance to in vivo gelling and other properties, these betides are considered to be particularly useful as antiovulatory agents and more generally to suppress the secretion of gonadotropins and inhibit the release of steroids by the gonads. Potentially even more important is the value of these betides for screening purposes because it can be predicted that certain comparable peptide analogs that are synthesized so as to have the comparable residue with a C$^\beta$-methyl substitution at this position would have potent properties, which might even be superior to that of the parent peptide. For example, in Example 3B, good biological results are obtained from which it is predicted that the corresponding β-methyl-containing analog would have good bioactivity. In fact, the comparable β-methyl analogs were synthesized, namely [Ac-βCH$_3$-D-2NAL$^1$, 4ClD-Phe$^2$, D-3PAL$^3$, Aph(atz)$^5$, D-Aph(atz)$^6$, ILys$^8$, D-Ala$^{10}$]-GnRH, with βCH$_3$-D-2NAL in both the E and T stereoisomer forms, and both were found to be fully active at 2.5 μg, with the E stereoisomer being partially active at 1.0 μg. Thus, the simple and straightforward betide synthesis avoids carrying out the lengthy and arduous synthesis of the analog having the residue with the C$^\beta$-methyl substitution by only performing such synthesis when the betide shows that such substitution would likely show significant improvement.

EXAMPLE 6

The peptide having the formula (cyclo 5-8)Ac-β-D-2NAL-(4Cl)D-Phe-D-3PAL-Ser-Glu-D-Arg-Leu-D/L-Agl(β-Ala)-Pro-D-Ala-NH$_2$ is synthesized using the general synthesis as set forth in Example 1. N$^\alpha$Boc-D/L-Agl(Fmoc) is coupled in the 8 position, and N$^\alpha$Boc-Glu(OFm) is coupled in the 5 position. In this synthesis, following the coupling of the first 5 residues, the following peptide intermediate is obtained: Boc-D-Arg-Leu-D/L-Agl(Fmoc)-Pro-D-Ala-NH-[MBHA resin support]. The side chain on the Agl residue is deprotected by removal of the Fmoc protection using 20 percent piperidine in DMF (10 ml) for about 30 minutes. After washing with DMF, the piperidine/DMF treatment is repeated. After a final wash with DMF, the intermediate is treated with N$^\alpha$Fmoc-β-Ala in DMF/DCM using DIC as a coupling reagent for about 30 minutes at room temperature to acylate the side chain of the Agl residue.

The betide resin is then subjected to the standard wash, and the synthesis is continued by removal of the Boc protection of D-Arg and next coupling N$^\alpha$Boc-Glu(OFm). The base-labile protecting groups on β-Ala and Glu are then removed as above, and the α-amino group of β-Ala is joined to the Glu residue side chain by reacting in the presence of BOP[Benzotriazolyl-N-oxytris(dimethylamino)-phosphorium hexafluorophosphate] and diisopropylethylamine. Thereafter, the completion of the synthesis and N-terminal acetylation are carried out as described hereinbefore. Cleavage from the resin and deprotection, followed by purification, are carried out as described in Example 1. The two stereoisomers are separated during the RP-HPLC. The two compounds (cyclo 5-8)Ac-β-D-2NAL-(4Cl)D-Phe-D-3PAL-Ser-Glu-D-Arg-Leu-γ-(beta-alanyl)D/L-amidoGly-Pro-D-Ala-NH$_2$ are each judged be homogeneous, and the purity of each is estimated to be greater than 80 percent. The optical rotations are measured on a photoelectric polarimeter as $[\alpha]_D^{20}$=−10.3° and −33.6°±1 (c=1, 50% acetic acid) respectively for the two isomers. MS analysis shows the expected mass of 1365.8 Da for both isomers.

Assaying the cyclic compound using the standard in vivo rat anti-ovulation test shows that, at a dosage of 25 micrograms, the first isomer is fully active while the second isomer is inactive; at a dosage of 10 micrograms, 3 out of 8 rats ovulate with the first isomer.

EXAMPLE 7

The somatostatin agonist betide having the structure: (cyclo 1-8)H-Cys-Phe-Phe-D/L-Agl(2-naphthoyl)-Lys-Thr-Phe-Cys-OH is synthesized by the following solid phase methodology in a stepwise manner on a chloromethylated resin. The resin is composed of fine beads (20–70 microns in diameter) of a synthetic resin prepared by copolymerization of styrene with one to two percent divinylbenzene. The benzene rings in the resin are chloromethylated in a Friedel-Crafts reaction with chloromethyl methyl ether and stannic chloride. The chlorine thus introduced creates a reactive benzyl chloride type of linker. The Friedel-Crafts reaction is continued until the resin contains 0.5 to 2 millimoles of chlorine per gram of resin.

The tert-butyloxycarbonyl-S-paramethoxybenzyl derivative of Cys, i.e. Boc-Cys(Mob), is linked to the resin by a known method, such as: (1) reflux in ethanol in presence of triethylamine, (2) cesium salt of the Boc-protected amino acid is kept at 50° C. in dimethylformamide (DMF) overnight or (3) Boc-protected amino acid is kept at 80° C. in dimethyl sulfoxide (DMSO) for 24 hours in the KF. One milliequivalent of the protected Cys per milliequivalent of Cl on the resin is used. Deprotection, neutralization and addition of each amino acid is performed in accordance with the schedules set forth in Example 1.

The Boc derivative of each amino acid is used. After deprotection of the first residue, i.e., Boc-Cys (Mob), according to the above schedule, the $N^\alpha$Boc derivative of Phe is added along with the coupling agent, dicyclohexylcarbodiimide (DCC). The $N^\alpha$Boc derivative of Thr is next added along with DCC, the side chain of Thr being protected with O-benzyl ether (Bzl). Benzyloxy-carbonyl-2Cl, i.e. 2ClZ, is used as the protecting group for the Lys side chain.

After the coupling of Boc-D/L-Agl(Fmoc) in the 4-position, the chain elongation process is interrupted to modify the side chain of Agl. The Fmoc protecting group is removed by treatment with 20 percent piperidine in DMF(10 ml.) for about 30 minutes; the intermediate is preferably washed with DMF and then treated with more piperidine/DMF for another 30 minutes. After preferably washing the peptidoresin with DMF, the newly freed amino groups are treated with 2 naphthoyl chloride in a mixture of NMP and diisopropylethylamine (DIPEA) for 1 hour. Alternatively, the $N^\alpha$Boc protection is first removed, the reaction with naphthoyl chloride is carried out, and then the Fmoc protection is removed to proceed with the chain elongation. The schedule is then used for the coupling of each of the three remaining amino acids of the peptide chain extending to Cys at the N-terminus.

Cleavage of the betide from the resin and deprotection of the side chain protecting groups of the betide are performed in hydrofluoric acid (HF) (50 ml) in the presence of 1 ml of anisole and 2 ml of dimethylsulfide for 1.5 hours at 0° C. After elimination of hydrofluoric acid under high vacuum, the resin-betide is washed with ether.

The resin is immediately extracted with 75% acetic acid (200 ml). The extract is filtered into a 500 milliliter round-bottom flask and stirred rapidly while adding a 10 weight percent solution of iodine in methanol until the resultant solution remains yellow-straw colored. It is then stirred for 10 additional minutes and quenched with 10% ascorbic acid in water until the yellow color is gone. Concentration under vacuum is carried out to reduce the volume to about 50 milliliters, followed by dilution to about 300 milliliters with 0.1% TFA in water. The solution is then applied to a 4 centimeter by 7 centimeter pad of $C_{18}$ silica in a coarse fritted funnel that was previously equilibrated with 0.1% TFA in water. Following vacuum filtration, the eluate is diluted to 1 liter and reapplied to the pad. Thereafter, the pad is washed with 500 milliliters of 6% acetonitrile in 0.1% TFA, and the betide is eluted using 250 milliliters of 60% $CH_3CN$ in water, followed by 150 milliliters of water. The resultant solution is diluted to about 600 milliliters, frozen and lyophilized.

The lyophilized material is then analyzed and purified by subjection to HPLC on a $C_{18}$ column. Peaks are located which are then individually purified using similar buffer systems. The desired cyclic betides (cyclo 1-8)H-Cys-Phe-Phe-(2-naphthylamido)Gly-Lys-Thr-Phe-Cys-OH (Betide No. 7) are obtained in the form of two separate stereoisomers which appear to be greater than 80% pure on capillary zone electrophoresis.

The specific optical rotations measure $[\alpha]_D^{22} = -50.5° \pm 1$: (c=0.875 in 50% acetic acid) for the first isomer and $-55.8° \pm (c=0.67$ in 50% acetic acid) for the second isomer, termed Betides 7 and 7'. Amino acid analysis of this material shows the expected ratio for the different amino acids. MS analysis shows the expected mass of 1119.5 Da.

EXAMPLE 7A

The synthesis described in Example 7 is repeated with one change. After coupling Boc-D/L-Agl(Fmoc), which is to constitute the 4-position residue, one of the two amino groups is methylated prior to its being reacted with naphthoyl chloride. For example, the Boc protecting group is removed by treatment with 60% TFA in DCM for about 20 minutes, providing the unprotected primary amino group. Alkylation of this primary amino group with 4,4'-dimethoxydityl chloride in the presence of diisopropylethylamine gives the corresponding N-terminal, secondary amino group containing the TFA-labile, 4,4'-dimethoxydityl group. Methylation of this secondary amine is carried out by treatment for 40 minutes with 36% aq. formaldehyde in NMP containing 1% HOAc (30:70) in the presence of excess sodium cyanoborohydride, which treatment is repeated. Thereafter, treatment with 60% trifluoroacetic acid in DCM (2×20 min.) removes the 4,4'-dimethoxydityl group and provides the corresponding $N^\alpha$-methylated residue which is then reacted with naphthoyl chloride. Further elongation of the chain then proceeds as in Example 7.

Cleavage, deprotection, cyclization and purification are carried out as in Example 7. The specific optical rotations measure $[\alpha]_D^{22} = -64.7° \pm 1$ (c=0.43 in 50% acetic acid) and $-24.0° \pm 1$ (c=0.57 in 50% acetic acid) respectively for the two isomers. MS analysis shows the expected mass of 1133.5 Da. The purified cyclic betides have the formula: (cyclo 1-8)H-Cys-Phe-Phe-(β-methyl-γ-2-naphthyl)D/L(amido)Gly-Lys-Thr-Phe-Cys-OH and are referred to as Betides Nos. 7A and 7A'.

EXAMPLE 8

In Examples 7 and 7A, cyclic octapeptides having somatostatin properties are synthesized, each of which has Lys in the 5-position. In this example, analogs are synthesized wherein a betidamino acid is employed instead of the lysine residue, and D-Trp is used in the 4-position. The synthesis described in Example 7 is repeated with respect to the first 3 residues. D/L-Agl(Fmoc), protected by $N^\alpha$Boc, is then coupled, followed by D-Trp, Phe, Phe and Cys(Mob), all protected by $N^\alpha$Boc. The Fmoc protecting group is removed as before by treating twice with 20 volume percent piperidine in NMP for 15 minutes each. The side chain primary amino group on the 5-position residue is then reacted with Boc-β-alanine to create a 5-position residue that mimics lysine.

Cleavage, deprotection, cyclization and purification are carried out as described in Example 7. The specific optical rotations measure $[\alpha]_D^{22}=-3.45°\pm1$: (c=0.725 in 50% acetic acid) and $-19.9°\pm1$ (c=0.67 in 50% acetic acid) respectively for the two isomers. MS analysis shows the expected mass of for each of the betide isomers of 1094.5.

The betides have the formula: (cyclo 1-8)H-Cys-Phe-Phe-D-Trp-γ-(2-aminoethyl)amido-glycine-Thr-Phe-Cys-OH, with one having the L-isomer in the 5-position and the other having the D-isomer, which are referred to as Betides Nos. 8 and 8'.

In vitro Bioassay: The effects of the various somatostatin analogs are tested in vitro for their ability to bind to isolated cloned receptors expressed on COS and CHO cells.

The molecular cloning of the genes encoding multiple somatostatin (SRIF) receptor subtypes has now permitted the individual expression of these receptors in mammalian cells and characterization of their respective pharmacological profiles. Five such receptor subtypes termed SSTR1 through SSTR5, have been cloned and are reported and described in Raynor et al., *Molecular Pharmacology*, 43, 838–844 (1993) and in Raynor et al., *Molecular Pharmacology*, 44, 385–392 (1993). These references describe binding assays that can be used to determine whether particular SRIF analogs bind selectively to one or more of the 5 receptor types and also whether they bind to such receptor types with high or low affinity. Because these receptor types have now been characterized with regard to their pharmacological profiles, knowledge of the results of such binding studies along with knowledge of the unique patterns of distribution of these receptors in the body indicate that each receptor subtype may mediate distinct but overlapping physiological effects of SRIF; therefore, compounds which bind selectively to one of those receptors can be used to modulate a particular physiological function of SRIF without potentially having an adverse effect upon another physiological function of SRIF.

The potencies of SRIF analogs, including the prior art compound ODT8, to inhibit radioligand binding to the cloned mouse SRIF receptors, relative to SRIF and SRIF-28, are shown in the following table wherein the $IC_{50}$ values are given in nanomolar concentration.

The production of betides in this manner and screening by the multiple SRIF receptors allows the synthesis of more effective peptides for selectively inhibiting secretion of growth hormone (GH), insulin and glucagon than somatostatin itself and which are also more effective than the parent (cyclo 1-8)ODT-8. For example, it can now be predicted that peptides having a comparable nonbetidamino residue to that in Betide No. 7A could be developed as SRIF analogs directed specifically to modulate the physiological function of the receptor SSTR3, whereas investigators would be spared from carrying out the lengthy and arduous syntheses of the peptides comparable to those in Examples 7 and 8 and which are predicted not to have good biological activity.

EXAMPLE 9

Human CRF is a 41-residue amidated peptide having the formula set forth in U.S. Pat. No. 4,489,163. One analog of this hormone which has been found to have greater biopotency than the native hormone for the release of ACTH is [D-Phe$^{12}$]-hCRF having the formula: H-Ser-Glu-Glu-Pro-Pro-Ile-Ser-Leu-Asp-Leu-Thr-D-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$.

It is desired to investigate the effect that substitution in the 22-position may have upon the biopotency of this CRF analog, and to efficiently carry out this investigation, a library of CRF analogs is created. First a peptide-resin intermediate having Agl at the 22-position is synthesized in a stepwise manner on MBHA hydrochloride resin beads. The synthesis is performed on an automatic Beckman 990B peptide synthesizer using a suitable program such as that set forth in Example 1.

Starting with BOC-Ile, the peptide chain is built step-by-step on the resin using an N$^\alpha$Boc protection strategy. Generally, one to two mmol. of Boc-protected amino acid in methylene chloride is used per gram of resin, plus one equivalent of 2 molar DCC in methylene chloride, for two hours. When Boc-Arg(Tos) is being coupled, a mixture of 50% DMF and methylene chloride is used. Bzl is used as the hydroxyl side-chain protecting group for Ser and Thr. P-nitrophenyl ester(ONp) can be used to activate the carboxyl end of Asn or Gln; for example, Boc-Asn(ONp) can be coupled overnight using one equivalent of HOBt in a 50% mixture of DMF and methylene chloride. The amido group

TABLE

| Compound | $IC_{50}$ | | | | |
|---|---|---|---|---|---|
| | mSSTR1 | mSSTR2 | mSSTR3 | mSSTR4 | mSSTR5 |
| SRIF | 0.10 | 0.28 | 0.08 | 0.86 | 1.2 |
| SRIF-28 | 0.07 | 0.43 | 0.07 | 0.23 | 0.29 |
| ODT8 | 1. | 35 | 4 | 0.9 | 2 |
| Betide No. 8 | >1000 | >1000 | >1000 | >1000 | >1000 |
| Betide No. 8' | >1000 | >1000 | >1000 | >1000 | >1000 |
| Betide No. 7A | >1000 | >1000 | 62 | >1000 | >1000 |
| Betide No. 7A' | 600 | >1000 | 200 | >1000 | 1300 |
| Betide No. 7 | >1000 | >1000 | >1000 | >1000 | >1000 |
| Betide No. 7' | >1000 | >1000 | >1000 | >1000 | >1000 |

Betides Nos. 7A and 7A' are shown to bind with some unusual selectivity as compared to SRIF and to the parent compound ODT-8, i.e., (cyclo 1-8)H-Cys-Phe-Phe-D-Trp-Lys-Thr-Phe-Cys-OH, as shown in the Table.

of Asn or Gln is protected by Xan when DCC coupling is used instead of the active ester method. 2-Cl-Z is used as the protecting group for the Lys side chain. Tos is used to protect the guanidino group of Arg and the imidazole group of His, and the side-chain carboxyl group of Glu or Asp is protected by OBzl. The second amino group of D/L-Agl is protected by Fmoc.

At the end of the synthesis, the following composition is obtained: Boc-Ser(Bzl)-Glu(OBzl)-Glu(OBzl)-Pro-Pro-Ile-Ser(Bzl)-Leu-Asp(OBzl)-Leu-Thr (Bzl)-D-Phe-His(Tos)-Leu-Leu-Arg(Tos)-Glu(OBzl)-Val-Leu-Glu(OBzl)-Met-D/L-Agl(Fmoc)-Arg(Tos)-Ala-Glu(OBzl)-Gln (Xan)-Leu-Ala-Gln(Xan)-Gln(Xan)-Ala-His(Tos)-Ser(Bzl)-Asn (Xan)-Arg(Tos)-Lys(2-Cl-Z)-Leu-Met-Glu(OBzl)-Ile-Ile-resin support. Xan may have been partially or totally removed by TFA treatment used to deblock the alpha-amino protecting groups.

A portion of the protected resin is then taken to synthesize one library of CRF analogs. For example, the Fmoc protection is removed using piperidine as described in Example 1 and then washed to provide the primary amino group as the side chain of the Agl residue in the 22-position. The beads are then distributed into 8 separate wells, and reaction is then carried out in each well with one of 8 commonly available chemical reactants. Each of the following is dissolved in a solution of DMF and allowed to react at room temperature for about 4 hours: benzoyl chloride, toluoyl chloride, 4-chloro-benzoyl chloride, acetic anhydride, isobutyric anhydride, benzyloxyacetyl chloride, beta-alanine pentafluorophenylester and indole 3-carboxyl-para-nitrophenylester. This eventually results in the creation of 16 different analogs (when starting with the D,L mixture of the aminoglycine) as a part of the betide resin. In order to cleave and deprotect the resulting protected betide-resin, it is treated with 1.5 ml. anisole, 0.5 ml. of methylethylsulfide and 15 ml. hydrogen fluoride(HF) per gram of betide-resin. Purification of each CRF analog uses preparative HPLC and is carried out in accordance with the teachings of U.S. Pat. No. 5,278,146 (Jan. 11, 1994), which eliminates salts, small fragments and hydrophobic impurities and ultimately separates the D and L isomers.

By testing the resultant 16 CRF analogs in the in vitro cultured rat pituitary cell assays as described in *Endocrinology*, 91, 562 (1972) and comparing the results against the native hormone, it is possible to obtain an indication as to whether any of these 16 analogs exhibits significant biopotency in this assay.

As an alternative library-building method, another portion of the protected resin is taken, deprotected as indicated, and then reacted with a mixture of the 8 previously specified chemical reactants. Following the reaction, the mixture of betides are similarly deprotected and cleaved from the resin and then a single purification of the entire mixture is carried out in the same general manner. Following purification, the entire mixture of 16 CRF analogs is tested for biopotency in the rat pituitary cell assay. If no biopotency is detected, it can be assumed that all 8 such substitutions at this position in the particular peptide sequence are ineffective, thus saving considerable time and effort in running 16 different assays. When such significant biopotency is detected, additional portions of the same peptide resin are used to create additional mixtures of analogs using fewer reactants, for example, two groups of 4 reactants each might next be created. The strategy is repeated until the analog or analogs responsible for the significant biopotency are determined.

Although only two representative working examples of use of the library concept are given, it should be understood that there are a variety of valuable alternatives that might be employed. For example, alkylation of an Agl residue or an Aal residue or an Asa residue using a plurality or a mixture of alkylating agents could be employed prior to acylating with a plurality or a mixture of acylating agents, or to the exclusion of subsequent acylation if it were desired to create a library of betoids for screening. Betoids are defined as peptides having at least one residue with a side chain amino group attached to the α-carbon that is substituted only by mono- or dialkylation; therefore, it resembles the corresponding peptoid. Instead of only including a single Agl or Aal or Asa residue, it is possible to include two-or more of such residues in a peptide and then simultaneously or independently acylate such residues using separate acylating agents or a mixture thereof. By selective deprotection, only one of such residues is reacted at a time. However, it is preferable to employ a SPPS strategy as described hereinbefore, either where multiple pins, plates or wells are used and programmed sequential reactions take place at different locations in the intermediate peptide-resin, or where resin beads are divided, reacted and recombined one or more times so that each bead carries betides of the same sequence.

Such methods of creating a plurality or a library of betides by synthesizing a single amino acid sequence including one or more differentially protected residues of Agl or Aal or Asa or Mdg or Mda is considered to be a valuable tool to permit the efficient screening of multiple prospective peptides for biopotency in one or more particular respects. Once the screening process detects a particular betide that has unique and desirable properties, the investigator can then more specifically test that betide and similar betides, as well as the equivalent peptides having only residues with natural or nonbetidamino unnatural side chains at the appropriate position or positions, as well as other modifications thereof, to discover the optimum configuration for enhancing such biopotency. Moreover, the use of multiple of these modular elements in a peptide sequence allows the generation of a nearly limitless number of oligomers from which one can select the best and, on the basis of it, synthesize the corresponding peptide using only natural or readily available α-amino acids. Thus, screenings of such chemically diverse libraries provide an efficient vehicle to provide leads that will result in new drug discoveries.

Although the invention has been described with regard to certain specific embodiments which constitute the best modes presently known to the inventors for carrying out the invention, it should be understood that various changes and modifications as would be obvious to one having the ordinary skill in the art may be made without departing from the scope of the invention which is defined by the claims appended hereto. For example, the α-amino group that is intended to form the amide bond to lengthen the peptide backbone can likewise be alkylated, as generally described herein (with regard to the amino group at the β-site), prior to carrying out the chain elongation step. This provides an efficient manner of screening for bioactivity or the like in peptides having $C^\beta$ alkylation, e.g. methylation, that are quite difficult to directly synthesize. Alternatively, by using Asa or Mdg or Mda instead of Agl, a residue having an N-methyl modification either in the side chain or in the backbone can be conveniently incorporated. Similarly, either of these alkylation steps can be carried out with a substituted ketone or the like so as to provide a substituted alkyl group instead of an unsubstituted alkyl as a part of the secondary amino moiety. Likewise, a wide variety of aminoreactive reagents can be employed to carry out the reaction at the β-site following the removal of the side chain protecting group; however, these acylating agents or other reactants, such as isocyanates and the like, are chosen so as to create an acid-stable and base-stable bond that will not be broken during subsequent synthesis steps and that will not be readily detached when subjected to normal physiological conditions in the body. Preferably, the bond to the β-site amino group should be such that the acylating agent cannot be selectively cleaved without subjecting the molecule to conditions that would cleave peptide bonds in the backbone.

Because certain non-natural α-amino acids are not commercially available and are difficult to synthesize, it is difficult to test whether such substitutions at a particular position in a peptide will enhance biopotency or the like. However, the invention provides a valuable method for screening the effects of such substitutions in peptides by preparing the corresponding betides with comparable betidamino acid residues at that position. Although screening may most commonly be carried out for biopotency, other properties such as binding affinity to receptors or other proteins, such as antibodies for example, may also be the subject of screening.

By employing differentially protected D/L-aminoglycine, $C^\alpha$-aminoalanine or aminosarcosine in the position in the peptide chain where the betide modification is desired, it is possible to simultaneously screen a variety of both D and L substituents for this position within a particular peptide. However, if it should be desired only to screen the D-isomers or the L-isomers, the racemic mixture of differentially protected D/L-aminoglycine, for example, can be optically resolved using a suitable procedure as known in the art, for example that disclosed by Kawai et al., *Optical Resolution of N-Carbobenzoxy-α-methoxyglycine, Tetrahedron: Asymmetry*, 3, 1019–1020 (1992).

Although the use of α-amino acids having differentially protected amino groups is preferred, (bis-Boc)Agl or (bis-Boc)Aal may alternatively be coupled into the chain. Thereafter, treatment with 1–5% TFA is used to deprotect only one amino group; the other is subsequently removed with 25% TFA at the desired time. Such is considered to be an equivalent of the preferred strategy of using differential protection for the two amino groups.

Although syntheses are described herein with respect to the preferred chain elongation processes wherein an α-amino-protected amino acid or peptide is added to the chain by reaction at its free α-carboxy group, it should be understood that chain elongation processes where the α-carboxy group is protected and reaction occurs at the free α-amino group are known and also considered to be equivalents thereof.

As earlier mentioned, once the scaffold is created by incorporating an Agl, Aal or Asa residue in a peptide chain, betoids can be alternatively created by only alkylating the side chain amino groups to create residues that resemble peptoids. The disclosures of all cited articles and patents are expressly incorporated herein by reference. Particular features of the invention are emphasized in the claims which follow.

What is claimed is:

1. A method for making a betide library using a chain elongation protocol, which method includes the steps of
    a) providing a resin or a peptide intermediate having an amino acid residue with a free α-amino group at the N-terminus thereof,
    b) providing an unnatural α-amino acid having the formula:

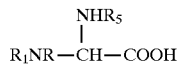

wherein R is H or lower alkyl, $R_1$ is a labile α-amino-protecting group, and $R_5$ is a labile amino-protecting group, $R_1$ and $R_5$ being respectively removable under conditions that do not cause the removal of the other;
    c) coupling said unnatural amino acid to said resin or to the N-terminus of said intermediate to extend the chain length thereof by one residue;
    d) removing $R_1$ and coupling at least one α-amino protected amino acid or peptide thereto or acylating the site of removal of $R_1$;
    e) removing $R_5$ from the product of step d; and
    f) creating a library of betides having different substituents upon said coupled unnatural amino acid by carrying out addition reactions, at the site of removal of $R_5$, with different amino-reactive reagents.

2. A method according to claim 1 wherein said amino-reactive reagent is selected from the group consisting of carboxylic acids, acyl halides, isocyanates, isothiocyanates and sulfonyl chlorides.

3. A method according to claim 1 wherein said resin is provided as a part of solid phase synthesis which creates peptidoresin material, wherein at least one additional said unnatural amino acid is coupled to the chain on said resin as a part of step d, wherein said peptidoresin material is distributed in a plurality of locations, wherein different of said amino-reactive reagents are caused to undergo said addition reactions with said peptidoresin material at at each said location, wherein $R_5$ is removed from said additional unnatural amino acid at each of said plurality of locations, and wherein said peptidoresin material at each said location is caused to each undergo a second addition reaction with a desired amino-reactive reagent at the site on said additional unnatural amino acid from which $R_5$ is removed.

4. A method according to claim 1 wherein said resin is employed in the form of beads of resin and at least one additional said unnatural amino acid is coupled to the peptide chain on said resin beads as a part of step d, wherein said resin beads are divided into a plurality of first portions and a different said reagent is caused to undergo a first addition reaction with each of said first portions of beads, wherein said first portions are combined and mixed following said first reactions, then divided into second portions of resin beads, and each of said second portions is caused to undergo a further addition reaction with a different amino-reactive reagent at a site on said additional unnatural amino acid from which $R_5$ is removed, whereby each said resin bead has coupled thereto betides of the same chemical structure.

5. A method for screening peptides for biopotency or the like, which method comprises the steps of
    making a library of betides corresponding to the peptides of interest according to the method of claim 1 using a mixture of said amino-reactive reagents,
    testing said mixed betide library for said desired property, and
    upon detecting biopotency in said betide mixture, repeating said library-making step at least twice, each time using mixtures containing fewer of said amino-reactive reagents than said first mixture and thereafter repeating said testing step.

6. A method for making a betide library containing a collection of different betides using a chain elongation solid phase peptide synthesis protocol, which method includes the steps of a) providing resin material in the form of either a resin having a site to which to couple the carboxyl group of an amino acid or a peptide-resin having an amino acid residue with a free α-amino group at the N-terminus of the peptide portion thereof, b) providing an unnatural α-amino acid having the formula:

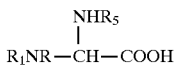

wherein R is H or lower alkyl, $R_1$ is a labile α-amino-protecting group, and $R_5$ is a labile amino-protecting group, $R_1$ and R5 being respectively removable under conditions that do not cause the removal of the other;

c) coupling said unnatural amino acid either to said resin or to the N-terminus of said peptide-resin to extend the length of the peptide chain thereof by one residue;

d) removing $R_1$ and either coupling at least one α-amino protected amino acid or peptide thereto to elongate the peptide chain or acylating the site of removal of $R_1$;

e) removing $R_5$ from the product of step d; and f) separately carrying out addition reactions with said coupled unnatural amino acid, at the site of removal of $R_5$, using different amino-reactive reagents at separate physical locations in order to create a library of betides having different substituents.

7. The method according to claim 6 wherein said amino-reactive reagents are selected from the group consisting of carboxylic acids, acyl halides, isocyanates, isothiocyanates and sulfonyl chlorides.

8. The method according to claim 7 wherein at least one additional said unnatural amino acid is coupled as a part of a chain on said resin material during step d, wherein said resin material is affixed to said separate locations where said different amino-reactive reagents are caused to undergo said addition reactions with said unnatural amino acid, wherein $R_5$ is then removed from said additional unnatural amino acid following said addition reactions, and wherein said peptide-resin material at each said separate location, at the site thereupon from which $R_5$ was removed from said additional unnatural amino acid, is caused to undergo a second addition reaction with another amino-reactive reagent.

9. A method according to claim 7 wherein said resin material is employed in the form of beads of resin and at least one additional said unnatural amino acid is coupled as a part of a peptide chain on said resin beads during step d, wherein said resin beads are initially divided into a plurality of first portions and a different said reagent is caused to undergo a first addition reaction with each of said first portions of beads, wherein said first portions of beads are combined and mixed following said first reactions and then divided into second portions, and said additional unnatural amino acid of each of said second portions is then caused to undergo an additional reaction with a different amino-reactive reagent at a site thereon from which $R_5$ is removed, whereby each said resin bead has coupled thereto betides of the same chemical structure.

10. A library containing a plurality of betides, each having the formula:

$X_N$-$X_1$-$X_2$-$X_3$-$X_m$-$X_4$-$X_5$-$X_6$-$X_C$, where $X_N$ is an acyl or other N-terminal group or a peptide up to about 50 amino acids in length having such an N-terminal group; $X_C$ is OH, $NH_2$ or other C-terminal group or a peptide up to about 50 amino acids in length having such a C-terminal group; $X_m$ is either des-X or a peptide up to about 50 amino acids, and $X_1$–$X_6$ are each independently des-X, a betidamino acid, a natural α-amino acid or an unnatural α-amino acid, provided however that at least one of $X_1$ to $X_6$ is a residue of a first betidamino acid of the formula:

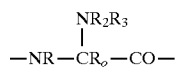

wherein $R_0$ is H or $CH_3$, R and $R_2$ are independently H or substituted or unsubstituted lower alkyl, and $R_3$ is an acyl group, an isocyanate group, a thioisocyanate group or a sulfonyl group; and that at least another of $X_1$ to $X_6$ is either a residue of an α-amino acid or a residue of a second different betidamino acid of the formula:

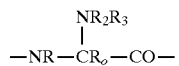

and provided further however that additional residues of betidamino acids can optionally be included in $X_n$, $X_m$ and $X_c$, each of said betides in said library being formed as a part of a single solid phase peptide synthesis wherein a peptide scaffold containing precursors of said betidamino acids is formed, and wherein a first set of portions of said scaffold are caused to undergo first addition reactions with reagents to incorporate a plurality of different $R_3$ groups into said betidamino acid residues of each of said first set of portions.

11. The library according to claim 10 wherein said betides in the library have a second different betidamino acid residue in which the $R_3$ group is different from the $R_3$ group of said first betidamino acid residue as a result of having undergone a second addition reaction with a different said reagent.

12. The library according to claim 10 wherein said betides are linked to separate resin substrates with all of the betides on a single resin substrate having the same formula.

* * * * *

UNITED STATES PATENT AND TRADEMARK OFFICE
CERTIFICATE OF CORRECTION

PATENT NO. : 5,807,986
DATED : September 15, 1998
INVENTOR(S) : Rivier, et al.

It is certified that error appears in the above-identified patent and that said Letters Patent is hereby corrected as shown below:

Column 20, line 24, "n" should be --in--.
Column 21, line 12, cancel all following the period and cancel line 13.

Column 32, line 20, insert --each-- after "wherein".
Column 33 (Claim 6), line 15, "R5" should be --$R_5$--.

Signed and Sealed this

Twelfth Day of January, 1999

Attest:

*Attesting Officer*    *Acting Commissioner of Patents and Trademarks*